United States Patent
Zergiebel

(10) Patent No.: US 9,259,221 B2
(45) Date of Patent: *Feb. 16, 2016

(54) MULTIPLE MEMBER INTERCONNECT FOR SURGICAL INSTRUMENT AND ABSORBABLE SCREW FASTENER

(71) Applicant: Covidien LP, Mansfield, MA (US)

(72) Inventor: Earl M. Zergiebel, Guilford, CT (US)

(73) Assignee: Covidien LP, Mansfield, MA (US)

( * ) Notice: Subject to any disclaimer, the term of this patent is extended or adjusted under 35 U.S.C. 154(b) by 365 days.

This patent is subject to a terminal disclaimer.

(21) Appl. No.: 13/623,373

(22) Filed: Sep. 20, 2012

(65) Prior Publication Data
US 2013/0018392 A1 Jan. 17, 2013

Related U.S. Application Data

(63) Continuation of application No. 12/706,159, filed on Feb. 16, 2010, now Pat. No. 8,292,933, which is a continuation of application No. 10/560,879, filed as application No. PCT/US2004/018702 on Jun. 14, 2004, now Pat. No. 7,670,362.

(60) Provisional application No. 60/478,352, filed on Jun. 13, 2003.

(51) Int. Cl.
*A61B 17/03* (2006.01)
*A61B 17/068* (2006.01)
(Continued)

(52) U.S. Cl.
CPC ............. *A61B 17/068* (2013.01); *A61B 17/064* (2013.01); *A61B 17/861* (2013.01);
(Continued)

(58) Field of Classification Search
CPC .. A61B 17/068; A61B 17/861; A61B 17/862; A61B 17/8635; A61B 17/864; A61B 17/866; A61B 17/8883; A61B 17/8891; A61B 31/148; A61B 17/064; A61B 17/869; A61B 2017/00004; A61B 2017/0648; A61B 17/08; A61L 31/06; A61L 31/148; B25B 13/481; B25B 17/00; B25B 23/065; B25B 23/101; C08L 67/04; Y10S 606/916
USPC ......... 606/139–143, 151–156, 312, 104, 916, 606/304, 308
See application file for complete search history.

(56) References Cited

U.S. PATENT DOCUMENTS

| | | |
|---|---|---|
| 2,033,039 A | 3/1936 | Limpert |
| 2,230,349 A | 2/1941 | Eaton et al. |

(Continued)

FOREIGN PATENT DOCUMENTS

| | | |
|---|---|---|
| DE | 10300787 A1 | 9/2004 |
| DE | 10 2010 015009 | 10/2011 |

(Continued)

OTHER PUBLICATIONS

Extended European Search Report corresponding to EP 14 15 9394.7, completed Apr. 16, 2014 and mailed Apr. 29, 2014; (8 pp).

(Continued)

*Primary Examiner* — Pedro Philogene

(57) ABSTRACT

An absorbable screw fastener and a method of firing with an applicator capable of applying a surgical fastener to tissue in order to form tissue connection to secure objects to tissue, the fastener including a body portion having a helical thread, a head portion disposed at the proximal end of the body portion. The head portion includes a driver receiving configuration on its outer surface. The screw fastener further includes a cannulated center lumen with an opening extending from the head portion through the longitudinal length of the body portion.

16 Claims, 23 Drawing Sheets

(51) Int. Cl.

| | | |
|---|---|---|
| *A61B 17/064* | (2006.01) | |
| *A61B 17/86* | (2006.01) | |
| *A61B 17/88* | (2006.01) | |
| *A61L 31/06* | (2006.01) | |
| *A61L 31/14* | (2006.01) | |
| *B25B 13/48* | (2006.01) | |
| *B25B 17/00* | (2006.01) | |
| *B25B 23/06* | (2006.01) | |
| *B25B 23/10* | (2006.01) | |
| *A61B 17/08* | (2006.01) | |
| *A61B 17/00* | (2006.01) | |

(52) U.S. Cl.
CPC ............ *A61B17/862* (2013.01); *A61B 17/864* (2013.01); *A61B 17/866* (2013.01); *A61B 17/8635* (2013.01); *A61B 17/8883* (2013.01); *A61B 17/8891* (2013.01); *A61L 31/06* (2013.01); *A61L 31/148* (2013.01); *B25B 13/481* (2013.01); *B25B 17/00* (2013.01); *B25B 23/065* (2013.01); *B25B 23/101* (2013.01); *A61B 17/08* (2013.01); *A61B 17/869* (2013.01); *A61B 2017/00004* (2013.01); *A61B 2017/0648* (2013.01); *Y10S 606/916* (2013.01)

(56) References Cited

U.S. PATENT DOCUMENTS

| | | | |
|---|---|---|---|
| 2,248,054 A | | 7/1941 | Becker |
| 3,866,510 A | | 2/1975 | Eibes et al. |
| 3,874,041 A | | 4/1975 | Smith |
| 3,882,756 A | | 5/1975 | Sauer et al. |
| 4,013,071 A | | 3/1977 | Rosenberg |
| 4,175,555 A | | 11/1979 | Herbert |
| 4,252,071 A | | 2/1981 | Rathert et al. |
| 4,285,292 A | | 8/1981 | Rathert et al. |
| 4,432,358 A | | 2/1984 | Fixel |
| 4,537,185 A | | 8/1985 | Stednitz |
| 4,644,957 A | | 2/1987 | Ricciardelli et al. |
| 4,658,825 A | | 4/1987 | Hochberg et al. |
| 4,756,653 A | | 7/1988 | Berger |
| 4,762,453 A | | 8/1988 | DeCaro |
| 4,815,909 A | | 3/1989 | Simons |
| 4,873,976 A | | 10/1989 | Schreiber |
| 4,884,572 A | | 12/1989 | Bays et al. |
| 4,895,148 A | | 1/1990 | Bays et al. |
| 4,976,715 A | | 12/1990 | Bays et al. |
| 4,994,073 A | | 2/1991 | Green |
| 5,053,047 A | | 10/1991 | Yoon |
| 5,169,400 A | | 12/1992 | Muhling et al. |
| 5,203,784 A | | 4/1993 | Ross et al. |
| 5,203,787 A | | 4/1993 | Noblitt et al. |
| 5,203,864 A | | 4/1993 | Phillips |
| 5,217,486 A | | 6/1993 | Rice et al. |
| 5,236,563 A | | 8/1993 | Loh |
| 5,246,441 A | | 9/1993 | Ross et al. |
| 5,258,000 A | | 11/1993 | Gianturco |
| 5,258,010 A | | 11/1993 | Green et al. |
| 5,263,974 A | | 11/1993 | Matsutani et al. |
| 5,312,023 A | | 5/1994 | Green |
| 5,342,397 A | | 8/1994 | Guido |
| 5,354,292 A | * | 10/1994 | Braeuer et al. .............. 606/1 |
| 5,382,260 A | | 1/1995 | Dormandy, Jr. et al. |
| 5,417,699 A | * | 5/1995 | Klein et al. ................. 606/144 |
| 5,429,641 A | | 7/1995 | Gotfried |
| 5,464,421 A | | 11/1995 | Wortrich |
| 5,475,063 A | | 12/1995 | Kaplan et al. |
| D366,113 S | | 1/1996 | Morgan |
| 5,522,817 A | | 6/1996 | Sander et al. |
| 5,582,616 A | * | 12/1996 | Bolduc et al. ............... 606/143 |
| 5,593,423 A | | 1/1997 | Person et al. |
| 5,607,095 A | * | 3/1997 | Smith et al. ............... 227/177.1 |
| 5,628,751 A | * | 5/1997 | Sander et al. ............... 606/104 |
| 5,690,676 A | | 11/1997 | DiPoto et al. |
| 5,725,529 A | | 3/1998 | Nicholoson et al. |
| 5,728,116 A | | 3/1998 | Rosenman |
| 5,730,744 A | | 3/1998 | Justin et al. |
| 5,733,307 A | | 3/1998 | Dinsdale |
| 5,827,291 A | | 10/1998 | Fucci et al. |
| 5,830,221 A | * | 11/1998 | Stein et al. .................. 606/157 |
| 5,868,749 A | | 2/1999 | Reed |
| 5,891,146 A | | 4/1999 | Simon et al. |
| 5,904,696 A | | 5/1999 | Rosenman |
| 5,928,244 A | | 7/1999 | Tovey et al. |
| 5,964,783 A | | 10/1999 | Grafton et al. |
| 5,971,985 A | | 10/1999 | Carchidi et al. |
| 5,997,552 A | * | 12/1999 | Person et al. ............... 606/139 |
| 6,027,523 A | | 2/2000 | Schmieding |
| 6,030,162 A | | 2/2000 | Huebner |
| 6,036,701 A | | 3/2000 | Rosenman |
| 6,045,560 A | | 4/2000 | McKean et al. |
| 6,063,112 A | | 5/2000 | Sgro |
| 6,066,777 A | | 5/2000 | Benchetrit |
| 6,096,060 A | | 8/2000 | Fitts et al. |
| 6,165,202 A | | 12/2000 | Kokish et al. |
| 6,171,330 B1 | | 1/2001 | Benchetrit |
| 6,214,031 B1 | | 4/2001 | Schmieding et al. |
| 6,228,954 B1 | | 5/2001 | Kaplan et al. |
| 6,235,869 B1 | | 5/2001 | Roby et al. |
| 6,248,108 B1 | | 6/2001 | Törmäläet al. |
| 6,264,702 B1 | | 7/2001 | Ory et al. |
| 6,296,656 B1 | | 10/2001 | Bolduc et al. |
| 6,319,270 B1 | | 11/2001 | Grafton et al. |
| 6,383,187 B2 | | 5/2002 | Törmäläet al. |
| 6,391,060 B1 | | 5/2002 | Ory et al. |
| 6,406,423 B1 | | 6/2002 | Scetbon |
| 6,408,656 B1 | | 6/2002 | Ory et al. |
| 6,443,964 B1 | | 9/2002 | Ory et al. |
| 6,450,391 B1 | | 9/2002 | Kayan et al. |
| 6,451,032 B1 | | 9/2002 | Ory et al. |
| 6,478,727 B2 | | 11/2002 | Scetbon |
| 6,508,830 B2 | | 1/2003 | Steiner |
| 6,533,454 B1 | | 3/2003 | Kaikkonen et al. |
| 6,537,312 B2 | | 3/2003 | Datta et al. |
| 6,547,801 B1 | | 4/2003 | Dargent et al. |
| 6,554,852 B1 | | 4/2003 | Oberlander |
| 6,562,051 B1 | | 5/2003 | Bolduc et al. |
| 6,565,580 B1 | | 5/2003 | Beretta |
| 6,569,186 B1 | | 5/2003 | Winters et al. |
| 6,575,897 B1 | | 6/2003 | Ory et al. |
| 6,596,002 B2 | | 7/2003 | Therin et al. |
| 6,666,854 B1 | | 12/2003 | Lange |
| 6,685,629 B2 | | 2/2004 | Therin |
| 6,692,506 B1 | | 2/2004 | Ory et al. |
| 6,695,855 B1 | | 2/2004 | Gaston |
| 6,755,836 B1 | | 6/2004 | Lewis |
| 6,840,953 B2 | | 1/2005 | Martinek |
| 6,929,661 B2 | | 8/2005 | Bolduc et al. |
| 7,128,754 B2 | | 10/2006 | Bolduc |
| 7,138,441 B1 | | 11/2006 | Zhang |
| 7,261,716 B2 | | 8/2007 | Strobel et al. |
| 7,582,107 B2 | | 9/2009 | Trail et al. |
| 7,588,587 B2 | | 9/2009 | Barbieri et al. |
| 7,670,362 B2 | * | 3/2010 | Zergiebel .................. 606/311 |
| 7,862,573 B2 | * | 1/2011 | Darois et al. .............. 606/151 |
| 8,002,811 B2 | | 8/2011 | Corradi et al. |
| 8,075,570 B2 | | 12/2011 | Bolduc et al. |
| 8,231,639 B2 | | 7/2012 | Bolduc et al. |
| 8,292,933 B2 | | 10/2012 | Zergiebel |
| 8,323,314 B2 | | 12/2012 | Blier |
| 8,343,184 B2 | | 1/2013 | Blier |
| 8,414,627 B2 | | 4/2013 | Corradi |
| 8,465,520 B2 | | 6/2013 | Blier |
| 8,597,311 B2 | | 12/2013 | Criscuolo |
| 8,728,120 B2 | | 5/2014 | Blier |
| 8,777,969 B2 | | 7/2014 | Kayan |
| 8,821,522 B2 | | 9/2014 | Criscuolo |
| 8,821,557 B2 | | 9/2014 | Corradi |
| 8,852,215 B2 | | 10/2014 | Criscuolo |
| 2001/0004694 A1 | | 6/2001 | Carchidi et al. |
| 2001/0007074 A1 | | 7/2001 | Strobel et al. |
| 2002/0013590 A1 | | 1/2002 | Therin et al. |
| 2002/0111641 A1 | | 8/2002 | Peterson et al. |

(56) References Cited

U.S. PATENT DOCUMENTS

| | | | |
|---|---|---|---|
| 2002/0177862 A1* | 11/2002 | Aranyi et al. | 606/153 |
| 2003/0004395 A1 | 1/2003 | Therin | |
| 2003/0009441 A1 | 1/2003 | Holsten et al. | |
| 2003/0036676 A1 | 2/2003 | Scetbon | |
| 2003/0036755 A1 | 2/2003 | Ginn | |
| 2003/0099102 A1 | 5/2003 | Duval | |
| 2003/0114839 A1 | 6/2003 | Looper et al. | |
| 2003/0158555 A1 | 8/2003 | Sanders et al. | |
| 2003/0187465 A1 | 10/2003 | Bailly et al. | |
| 2004/0049196 A1 | 3/2004 | Jackson | |
| 2004/0068267 A1* | 4/2004 | Harvie et al. | 606/92 |
| 2004/0076924 A1 | 4/2004 | Kim | |
| 2004/0092937 A1 | 5/2004 | Criscuolo et al. | |
| 2004/0111089 A1 | 6/2004 | Stevens et al. | |
| 2004/0127916 A1 | 7/2004 | Bolduc | |
| 2004/0181222 A1 | 9/2004 | Culbert et al. | |
| 2004/0243139 A1 | 12/2004 | Lewis et al. | |
| 2004/0254608 A1 | 12/2004 | Huitema et al. | |
| 2006/0124688 A1 | 6/2006 | Racenet et al. | |
| 2006/0217727 A1 | 9/2006 | Munro et al. | |
| 2006/0273135 A1 | 12/2006 | Beetel | |
| 2006/0291981 A1 | 12/2006 | Viola et al. | |
| 2008/0147113 A1 | 6/2008 | Nobis | |
| 2008/0188868 A1 | 8/2008 | Weitzner | |
| 2008/0243106 A1 | 10/2008 | Coe et al. | |
| 2008/0281336 A1 | 11/2008 | Zergiebel | |
| 2008/0312687 A1 | 12/2008 | Blier | |
| 2009/0188965 A1 | 7/2009 | Levin | |
| 2010/0030262 A1 | 2/2010 | McClean | |
| 2011/0022065 A1 | 1/2011 | Shipp | |
| 2011/0060349 A1 | 3/2011 | Cheng | |
| 2011/0071578 A1 | 3/2011 | Colesanti | |
| 2011/0079627 A1 | 4/2011 | Cardinale | |
| 2011/0087240 A1 | 4/2011 | Shipp | |
| 2011/0295282 A1 | 12/2011 | Glick | |
| 2012/0059397 A1 | 3/2012 | Criscuolo | |
| 2012/0109157 A1 | 5/2012 | Criscuolo | |
| 2013/0018392 A1 | 1/2013 | Zergiebel | |
| 2013/0110088 A1 | 5/2013 | Wenchell | |
| 2013/0131700 A1 | 5/2013 | Criscuolo | |
| 2013/0197591 A1 | 8/2013 | Corradi | |
| 2014/0114329 A1 | 4/2014 | Zergiebel | |
| 2014/0121684 A1 | 5/2014 | Criscuolo | |
| 2014/0276967 A1 | 9/2014 | Fischvogt | |
| 2014/0276969 A1 | 9/2014 | Wenchell | |
| 2014/0276972 A1 | 9/2014 | Abuzaina | |
| 2014/0316446 A1 | 10/2014 | Kayan | |
| 2014/0371765 A1 | 12/2014 | Corradi | |
| 2015/0001272 A1 | 1/2015 | Sniffin | |
| 2015/0005748 A1 | 1/2015 | Sniffin | |
| 2015/0005788 A1 | 1/2015 | Sniffin | |
| 2015/0005789 A1 | 1/2015 | Sniffin | |
| 2015/0018847 A1 | 1/2015 | Criscuolo | |
| 2015/0032130 A1 | 1/2015 | Russo | |
| 2015/0080911 A1 | 3/2015 | Reed | |
| 2015/0133970 A1 | 5/2015 | Ranucci et al. | |
| 2015/0133971 A1 | 5/2015 | Ranucci et al. | |
| 2015/0133972 A1 | 5/2015 | Ranucci et al. | |

FOREIGN PATENT DOCUMENTS

| | | | |
|---|---|---|---|
| EP | 0 834 280 A1 | | 4/1998 |
| EP | 1 025 803 A1 | | 8/2000 |
| EP | 199037 A2 | | 4/2002 |
| EP | 1273272 A2 | | 1/2003 |
| EP | 1 293 168 A2 | | 3/2003 |
| EP | 1908409 | | 4/2008 |
| EP | 1990013 A1 | | 11/2008 |
| EP | 2055241 | | 5/2009 |
| EP | 2399538 A2 | | 12/2011 |
| EP | 2484294 | | 8/2012 |
| JP | 09 149906 A | | 6/1997 |
| WO | WO98/11814 A2 | | 3/1998 |
| WO | WO 00/16701 | | 3/2000 |
| WO | WO 01/62136 A2 | | 8/2001 |
| WO | WO 01/97677 A2 | | 12/2001 |
| WO | WO 02/30296 A2 | | 4/2002 |
| WO | WO 02/34140 | | 5/2002 |
| WO | WO 02/091932 A1 | | 11/2002 |
| WO | WO 03/034925 A2 | | 5/2003 |
| WO | WO 03/049906 A2 | | 6/2003 |
| WO | WO 03/103507 | | 12/2003 |
| WO | WO 2004/112841 A2 | | 12/2004 |
| WO | WO 2004/112841 A3 | | 12/2004 |
| WO | WO 2005/004727 | | 1/2005 |
| WO | WO 2012/064692 | | 5/2012 |
| WO | 2013/046115 A1 | | 4/2013 |

OTHER PUBLICATIONS

European Search Report for EP10012659—completion date Dec. 21, 2010 (3 pages).

European Search Report for EP10012646.5-2310—completion date Feb. 11, 2011 (3 pages).

European Search Report from European Application No. EP 08 25 1988, dated Sep. 19, 2008; 2 pages.

European Search Report from European Application No. EP 04 75 5078, dated Jul. 2, 2008; 7 pages.

European Search Report from European Application No. EP 08 00 4478, dated May 16, 2008; 8 pages.

European Search Report from European Application No. EP 06 00 8305, date of "Extended" European Search Report is Nov. 28, 2006; 5 pages.

International Search Report from International Application No. PCT/US04/18702, dated Jun. 3, 2005; 2 pages.

Extended European Search Report corresponding to EP 14 15 8946.5, completed Jun. 20, 2014 and mailed Jul. 8, 2014; (9 pp).

Extended European Search Report corresponding to EP 14 17 8107.0, completed Nov. 24, 2014 and mailed Dec. 3, 2014; (5 pp).

Extended European Search Report corresponding to EP 14 17 4656.0, completed Jan. 16, 2015 and mailed Jan. 26, 2015; (7 pp).

Extended European Search Report corresponding to EP 14 18 4907.5, completed Jan. 12, 2015 and mailed Jan. 27, 2015; (9 pp).

Extended European Search Report corresponding to counterpart application EP 14 19 7885.8 dated Mar. 30, 2015; 9pp.

Extended European Search Report corresponding to counterpart application EP 14 18 1900.3 dated Apr. 9, 2015; 7pp.

* cited by examiner

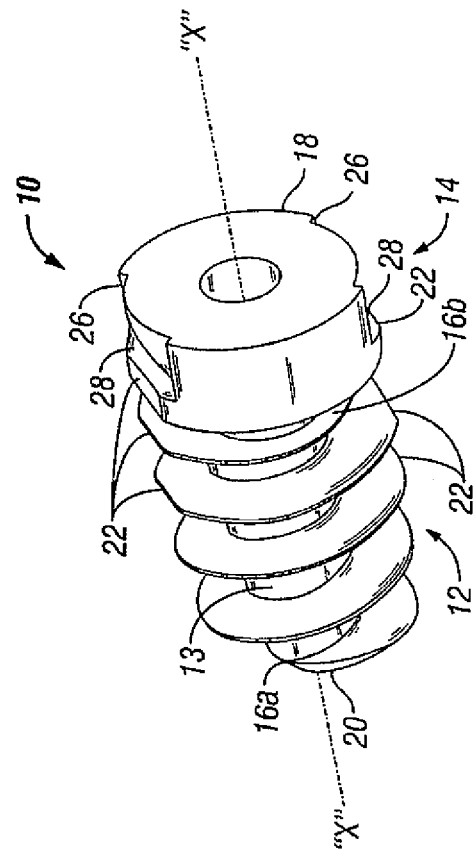
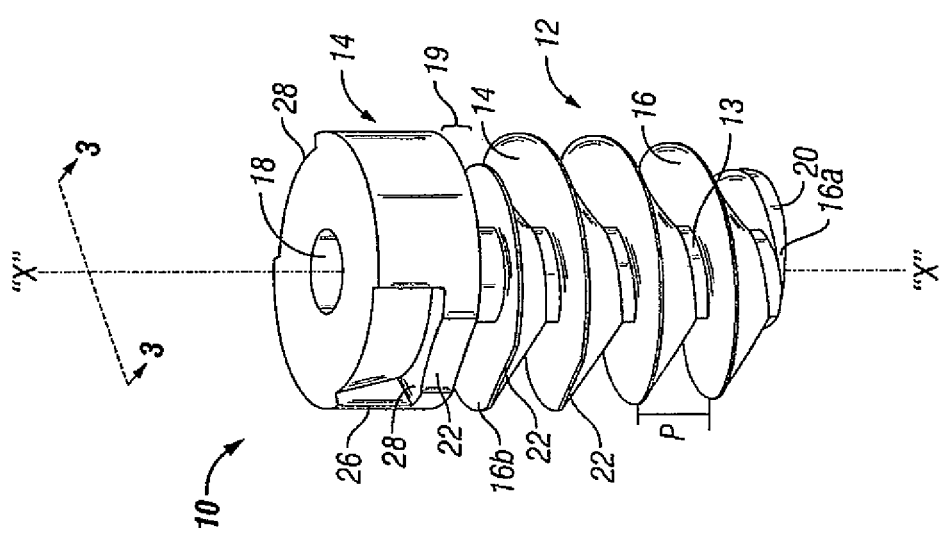

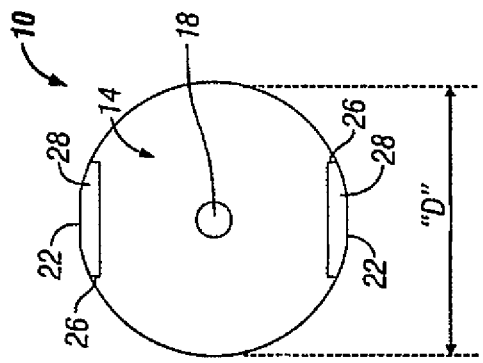
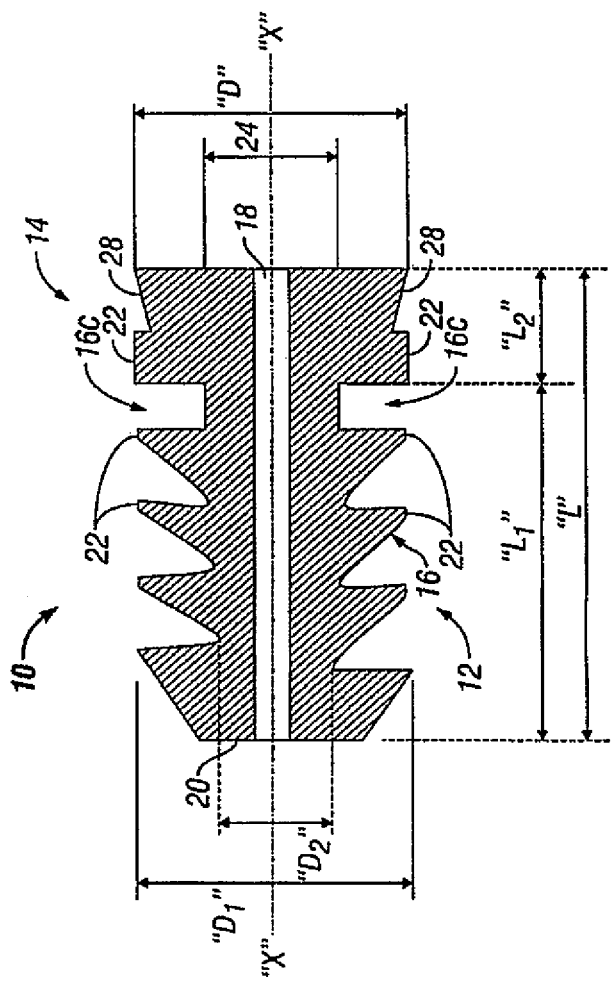
FIG. 4
FIG. 3

MULTIPLE MEMBER INTERCONNECT FOR SURGICAL INSTRUMENT AND ABSORBABLE SCREW FASTENER

CROSS REFERENCE TO RELATED APPLICATIONS

This application is a Continuation Application claiming the benefit of and priority to U.S. application Ser. No. 12/706,159, filed on Feb. 16, 2010, which is a Continuation Application claiming the benefit of and priority to U.S. application Ser. No. 10/560,879, filed on May 10, 2006 (now U.S. Pat. No. 7,670,362), which claims the benefit of and priority to International Patent Application PCT/US2004/018702, filed on Jun. 14, 2004, which claims the benefit of and priority to U.S. Provisional Patent Application Ser. No. 60/478,352, filed on Jun. 13, 2003, the disclosures of which are incorporated herein in their entirety by this reference.

BACKGROUND OF THE INVENTION

1. Technical Field

The present disclosure relates generally to surgical fasteners, surgical fasteners appliers and methods for connecting body tissue and, more particularly, to bio-absorbable screw fasteners, screw fastener appliers, and methods of using the screw fastener applier to fire multiple absorbable screw fasteners to a target surgical site.

2. Description of Related Art

Surgical fasteners are used to eliminate the need for suturing, which is often time consuming and inconvenient. Surgical fasteners accomplish in seconds what would have taken many minutes to accomplish by suturing, thus reducing operating time and trauma to the patient. In hernia repair procedures, for example, the weakened area of the abdominal wall may be reinforced with a synthetic mesh or by suturing the abdominal tissue. In such an instance, a surgical fastener in the form of an absorbable screw fastener may be used, in lieu of or in addition to, a surgical suture to fix the position of the mesh.

In view of the widespread use of surgical fasteners, a continuing need exists for improved surgical fasteners, surgical fastener appliers, and methods of applying the surgical fasteners.

SUMMARY

Accordingly, the present disclosure relates to an absorbable screw faster to form tissue connections, the absorbable screw fastener having a head configuration which permits the use of a combined rotational force and linear force to facilitate insertion. The absorbable screw fastener is tacked into body tissue to form tissue connection to secure objects such as a mesh material to tissue.

In one embodiment, the absorbable screw fastener includes a body portion having a helical thread, a head portion disposed at the proximal end of the body portion and a blunt end at a distal portion of the body portion. The head portion includes a driver receiving configuration on its outer diameter, said driver receiving configuration is used to transmit both linear and rotational forces in order to drive the absorbable screw fastener. The absorbable screw fastener may be bioabsorbable. The body portion of the bioabsorbable fastener is threaded, with the spacing between adjacent threads being augmented to provide a wider pitch. In addition, the thread's outer diameter is enlarged creating substantially more land, giving the absorbable screw fastener greater stability and preventing dislodgement from the body tissue. The absorbable screw fastener includes a cannulated center lumen with an opening extending from the head portion through the longitudinal length of the body portion of the absorbable fastener. The head portion may also include a flat segment, which may further extend to the outside of the threads.

The subject of the invention achieves several very significant advantages over the prior art. The low profile of the head portion (about 1.5 mm compared to about 5 mm of the body portion) reduces adhesion to the body tissue. The pitch configuration and the land created by enlarging the outer diameter of the thread enable the fastener to resist dislodgement. Finally, the driver receiving configuration on the head portion allows for torque and linear drive thus allowing for considerably less insertion force into the body tissue.

Other features and advantages of the present invention will become apparent from the following detailed description, taken in conjunction with the accompanying drawings, which illustrate, by way of example, the principals of the invention.

BRIEF DESCRIPTION OF THE DRAWINGS

Embodiments of the present disclosure will be better appreciated by reference to the drawings wherein:

FIG. 1 is a perspective view of an absorbable screw fastener in accordance with an embodiment of the present disclosure;

FIG. 2 is another perspective view of the absorbable screw fastener of FIG. 1;

FIG. 3 is a longitudinal cross-sectional view of the absorbable screw fastener of FIG. 1 taken along line 3-3 of FIG. 1;

FIG. 4 is an orthogonal top view of the absorbable screw fastener of FIG. 3;

DETAILED DESCRIPTION OF THE EMBODIMENTS

Figure 5:
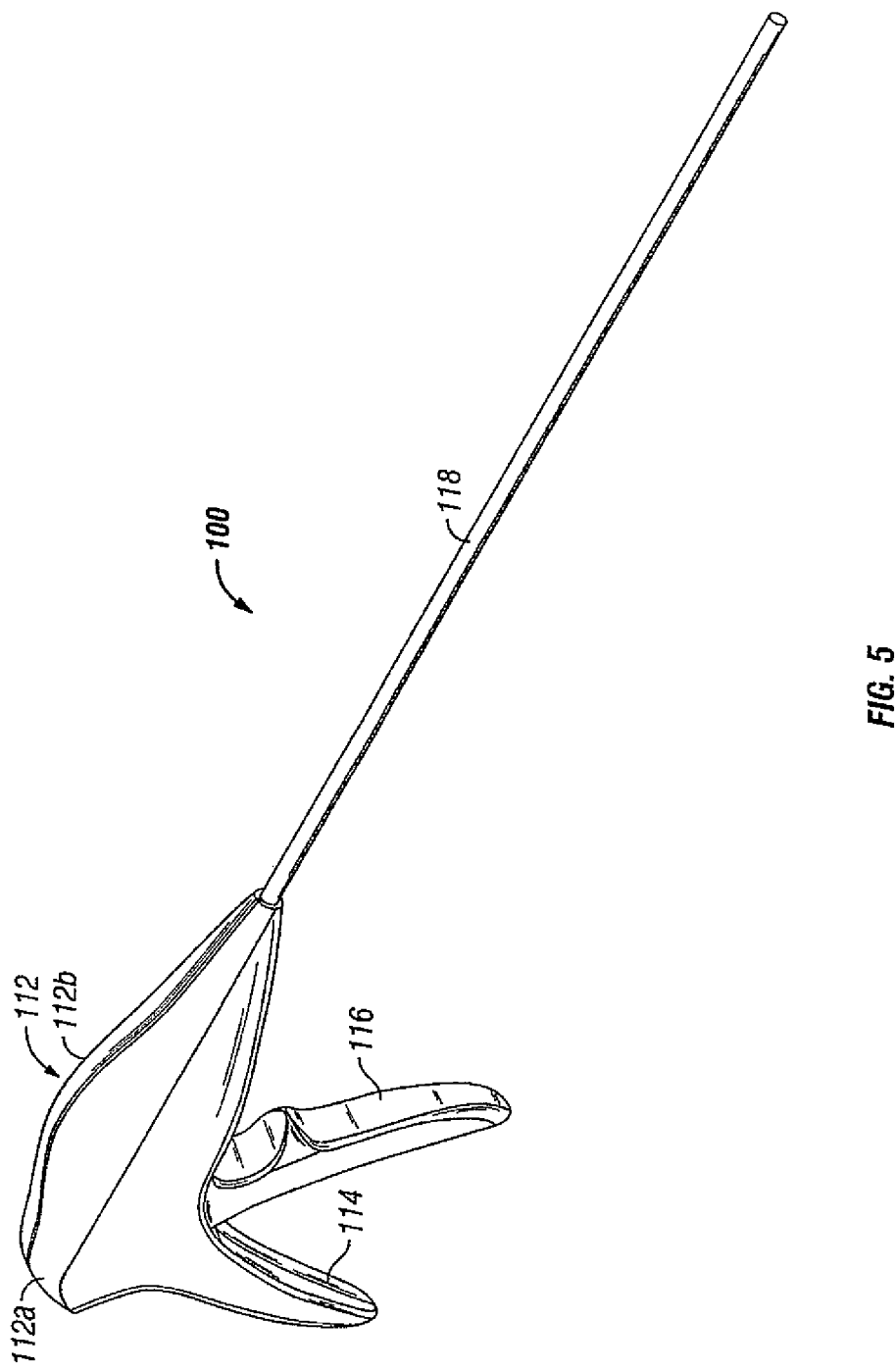
FIG. 5 is a perspective view of an embodiment of a screw fastener applier according to an embodiment of the present disclosure.

Referring now in detail to the figures, which are included for purposes of illustration and not by way of limitation, an absorbable screw fastener of the present disclosure is illustrated in FIGS. 1-4, and is designated generally as absorbable screw fastener 10.

The presently disclosed embodiments of absorbable screw fastener 10 contemplate the insertion of an absorbable screw fastener through a trocar into various tissue types using minimal application of force. Tissue typically wicks into the mesh in about 7-10 days, meaning that the fastener must maintain a certain structural integrity for at least that amount of time. Desirably, absorbable screw fastener 10 is constructed so as to maintain its structural strength by about 80% for about 10-21 days. Thereafter, the tissue will grow into the mesh and the absorbable screw fastener 10 will be absorbed by the body at a fixed rate leaving in place only the mesh.

Although the specific focus of this disclosure will be on a laparoscopic hernia repair, it will be noted that hernia repair is merely representative of a type of surgical procedure wherein absorbable screw fastener 10 can be utilized.

In the following description, as is traditional, the term "proximal" refers to the portion of the screw, applier or instrument closest to the operator, while the term "distal" refers to the portion of the screw, applier or instrument remote from the operator.

Referring now to FIGS. 1-4, absorbable screw fastener 10 includes two main components, namely a body portion 12 defining a longitudinal axis "X" and a substantially circular head portion 14 disposed on a proximal end of body portion 12. Absorbable screw fastener 10 further includes a central cannulated opening or lumen 18 extending along the longitudinal "X" axis of body portion 12 and head portion 14 for receiving a mating part therein, as will be described in greater detailed below. In one embodiment, cannulated lumen 18 has a hexagonal traverse cross-sectional profile (not shown). Alternatively, it is envisioned that cannulated lumen 18 may have a circular, rectangular or triangular traverse cross-sectional profile.

Body portion 12 includes a helical thread 16 extending along a length thereof, and may also include a truncated or blunt distal end 20. Further body portion 12 includes a center shaft 13 extending along a length thereof. Center shaft 13 and/or may have a constant outer distance D1 and D2, or may taper from a larger proximal end to a smaller distal end.

In one embodiment, head portion 14 has a distance "D" (of about 3.51 mm) which is approximately 54% of an overall length "L" (of about 6.5278 mm) of screw fastener 10. Additionally, body portion 12 has a length "L1" which is approximately 70-80% of the overall length "L" of screw fastener 10. In another embodiment, length "L1" is about 77% of the overall length "L". For example, head portion 14 may have a height or length "L2" of about 1.5 mm and body portion 12 may have a length "L1" of about 5.0 mm. In yet another embodiment, distance "D" of head portion 14 is substantially equal to an outer distance "D1" of body portion 12 and helical thread 16.

The dimensions and physical characteristics of absorbable screw fastener 10 are selected to insure a secure attachment of screw fastener 10 to tissue. Similarly, the dimensions and physical characteristics of applicator 100 (FIG. 5) utilized to dispense screw fastener 10 into tissue are dependent upon the particular application.

With continued reference to FIGS. 1-4, head portion 14 includes driver receiving recesses or structure, in the form of slots 28, formed in an outer radial surface of head portion 14. Slots 28 are configured to transmit torque to screw fastener 10. In one embodiment, a pair of diametrically opposed slots 28 are formed in head portion 14. Additionally, each slot 28 may be tapered at an angle toward the longitudinal "X" axis extending distally from a proximal surface head portion 14. The taper of slots 28 helps to facilitates rotation and driving of screw fastener 10. Alternatively or additionally, it is envisioned that a torque transmitting feature may be provided on slots 28, in the form of shoulders 26, or on the centrally cannulated opening 18, in the form of a keyed surface (not shown). As described herein, the torque transmitting feature allows for screw fastener 10 to be rotated.

With particular reference to FIG. 3, body portion 12 includes a single continuous helical thread 16 thereon. Thread 16 includes an outer distance "D1" which is substantially enlarged as compared to an inner distance "D2" thereof. Having a substantially enlarged outer distance "D1" as compared to inner distance "D2" enables the tissue to more fully and intimately adhere to the surface of screw fastener 10, consequently reducing instances of dislodgement of screw fastener 10. Thread 16 has a pitch "P" (as seen in FIG. 1) between adjacent individual threads.

Thread 16 is also desirably tapered at both a distal lead-in 16a and a proximal run-out 16b. A space or gap 16c is provided between proximal thread run-out 16b and a distal surface of head portion 14. Gap 16c allows for the surgical mesh to rest therein. It is envisioned that the pitch of thread 16 may be larger or smaller depending on the particular surgical procedure. Additionally, the cross-sectional shape of thread 16 may be triangular, rectangular, etc.

As seen in FIGS. 1-4, screw fastener 10 may include at least one pair (three pairs shown) of diametrically opposed planer or flattened surfaces 22 formed in the outer radial surface of head portion 14 and helical thread 16. Each planar surface 22 may additionally be in radial registration with a respective slot 28. Planar surface 22 extends distally from head portion 14 to helical thread 16 of body portion 12 and substantially along the entire length of body portion 12. Planar surface 22 is provided for orientation of screw fastener 10 inside fastener applier 100, as will be described in detail below. It is envisioned that other features may be provided for orientation of screw fastener 10 inside fastener applier 100.

Screw fasteners 10 may be fabricated from a medical bio-absorbable material such as for example, and not limited to, polyglycolic acid or poly-Glycolide (PGA) and/or polylactic acid (PLA), L1 (18/82 poly-Glycolide-co-L-lactide), L4 (42/58 poly-Glycolide-co-L-lactide), PGB (63/37 poly-Glycolide-co-Trimethylene Carbonate), any other biocompatible implantable material, or any combinations thereof. Screw fasteners 10 may be fabricated from a bio-absorbable material which ensures that screw fastener 10 maintains its structural integrity (e.g., about 80% of original strength) for a predetermined period of time, such as, for example, approximately 10 days. It is further contemplated that screw fastener 10, or a portion thereof, be coated with a biocompatible material such as parylene, that may also be lubricious, and that provides for easier delivery of screw fastener 10 into tissue. But, more importantly, creating a longer absorption time of the surgical fastener 10. Typically, such screw fasteners 10 are formed using an injection molding process as would be understood by one skilled in the art.

Desirably, absorbable screw fastener 10 may be delivered within an endoscopic 5 mm-diameter shaft of a fastener applier capable of firing multiple fasteners. Components of an applier that may be used in the firing of absorbable screw fasteners is shown and described in U.S. Pat. No. 5,830,221, the entire disclosure of which is incorporated herein by reference.

Figure 6:
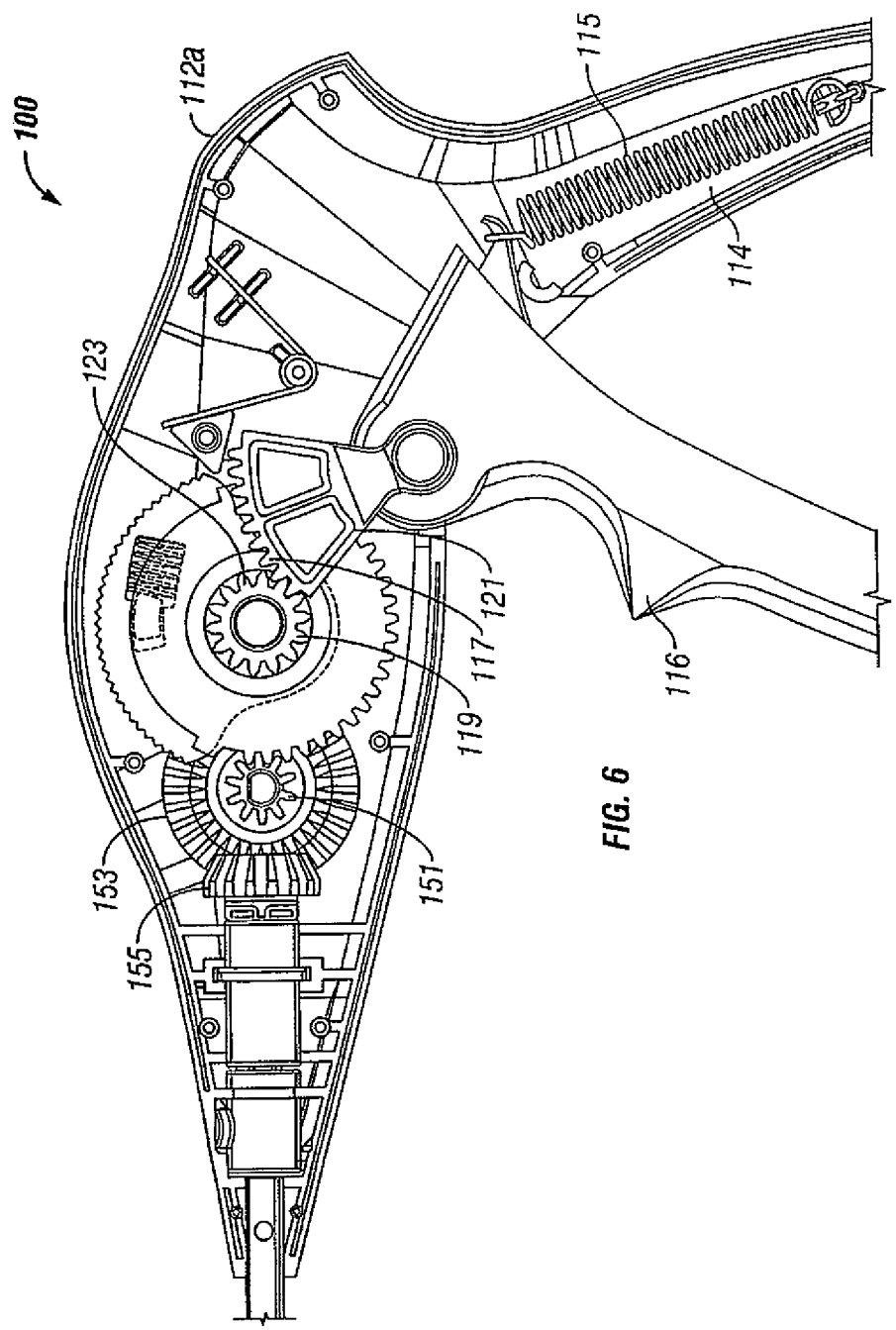
FIG. 6 is a side view, with a housing half removed, of the housing portion of the screw fastener applier of FIG. 5 while in an initial position.

Referring now to FIGS. 5 and 6, a fastener applier for applying absorbable screw fasteners 10 is shown generally as fastener applier 100. Fastener applier 100 generally includes a proximal housing portion 112, which may be formed as two separate housing halves 112a and 112b and a handle portion 114 extending from housing 112. A trigger 116 is movably mounted to housing 112. Trigger 116 may be pivotally connected to housing 112 with a free end of trigger 116 spaced from a free end of handle portion 114. This arrangement provides an ergonomic advantage and positive secure control of trigger 116 and fastener applier 100. Fastener applier 100 also includes an elongated tubular portion 118 extending distally from housing 112. The elongated tubular portion 118 is provided to retain a plurality of screw fasteners 10 for application to body tissue. Elongated tubular portion 118 is dimensioned to fit through conventional endoscopic tubes or cannula structures inserted through small incisions in the body. In general, manipulation of control trigger 116 results in ejection of screw fasteners 10, one by one, out of elongated tubular portion 118 and into body tissue.

Figure 8:
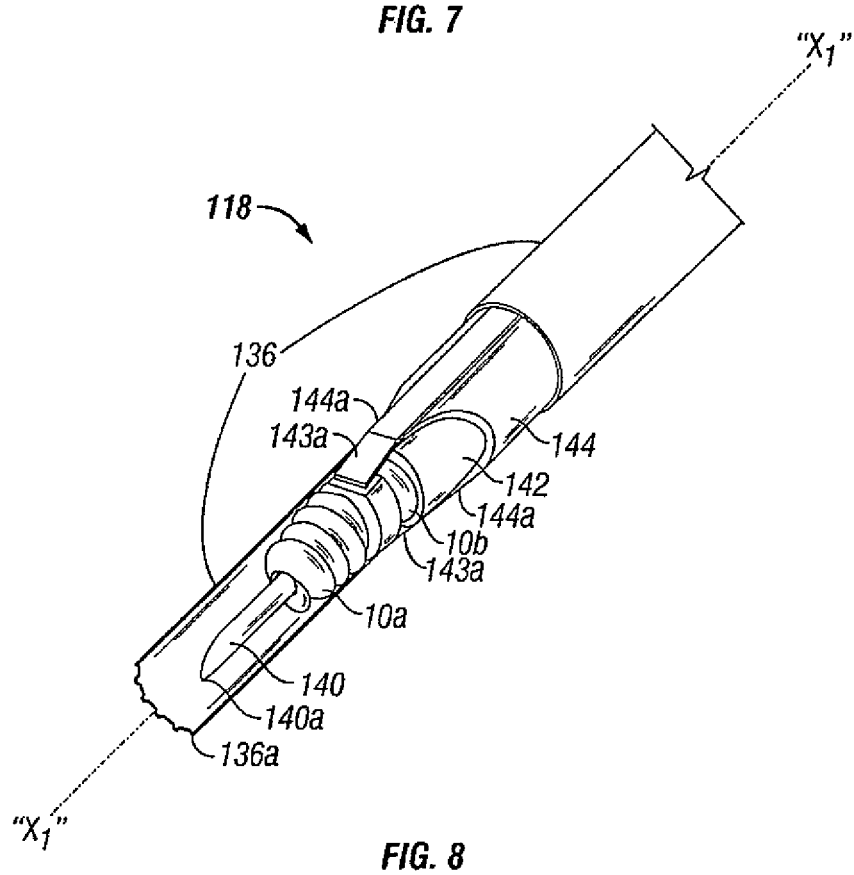
FIG. 8 is a perspective partial cross-sectional view of the distal end of the screw fastener applier of FIGS. 5 and 6.

With continued reference to FIG. 6, operation of housing portion 112 of fastener applier 100 is described. In an initial or starting position, trigger 116 is biased away from handle 114 due to the force of return spring 115. As shown, teeth 117 of gear portion 121 of trigger 116 are engaged with teeth 119 of trigger gear 123. As trigger 116 is squeezed, teeth 117 engage teeth 119 of trigger gear 123 to rotate driver gear 151, which, in turn, rotates a first bevel gear 153 which, in turn, rotates a bevel drive gear 155 and ultimately cylindrical driver 144, fastener retainer 142 and pilot 140 (as seen in FIG. 8). Reference may be made to U.S. Pat. No. 5,830,221, previously incorporated herein by reference, for a detailed discussion of the operation of housing portion 112 of fastener applier 100.

Figure 7:
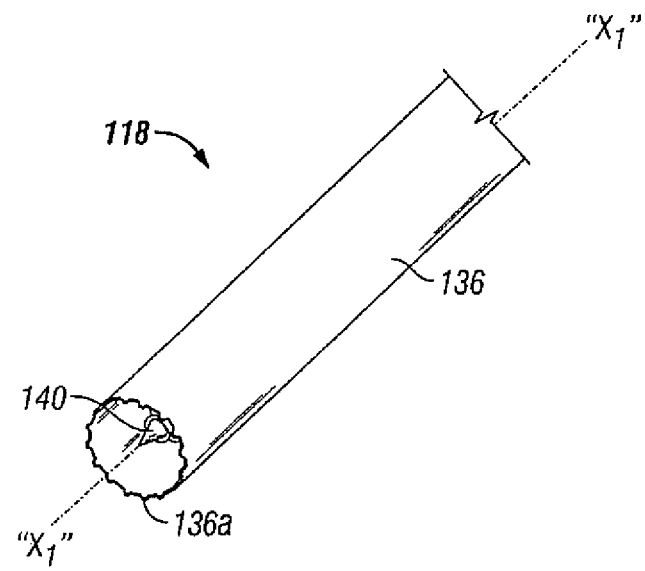
FIG. 7 is a perspective view of a distal end of the screw fastener applier of FIG. 5.

Referring to FIGS. 7-8, elongated tubular portion 118 includes an outer tube 136, defining a longitudinal axis "X1" and housing a cylindrical driver 144. Cylindrical driver 144 generally includes a longitudinally extending pilot 140, and a cylindrical fastener retainer 142 extending along the length of cylindrical driver 144. Fastener retainer 142 is configured to receive a plurality of screw fasteners 10 and pilot 140 therein, such that upon rotation of cylindrical driver 144, screw fasteners 10 and pilot 140 are similarly rotated. A plurality of screw fasteners 10 may be arranged in a series longitudinally along the length of a distal portion of cylindrical driver 144. Each screw fastener 10 is positionable within fastener retainer 142 of cylindrical driver 144.

Cylindrical driver 144 includes a pair of opposed resilient fingers or tabs 144a extending from a distal-most end thereof. Each resilient finger 144a includes a distal tip 143a angled and/or otherwise oriented toward the longitudinal "X1" axis. As seen in FIG. 8, resilient fingers 144a of cylindrical driver 144 hold or pinch a distal-most screw fastener 10a in position ready for application. In particular, distal tip 143a of each resilient finger 144a of cylindrical driver 144 is seatable in or receivable in respective slots 28 formed in head portion 14 of screw fastener 10 (see for instance FIG. 1). In operation, cylindrical driver 144 functions to engage a plurality of fasteners and to facilitate turning and driving/advancing of screw fasteners 10 into tissue.

Outer tube 136 may additionally be provided with a crenellated distal tip 136a for engaging mesh overlying the surgical site in order to maintain the mesh firmly in position and prevent the mesh from thrusting or otherwise spinning or bunching while absorbable screw fastener 10 is torqued and driven through the mesh. Crenellated distal tip 136a, of outer tube 136, may be of various geometric shapes and dimensions, (e.g., serrated, saw-toothed, etc.), or may be omitted completely.

Figure 9:
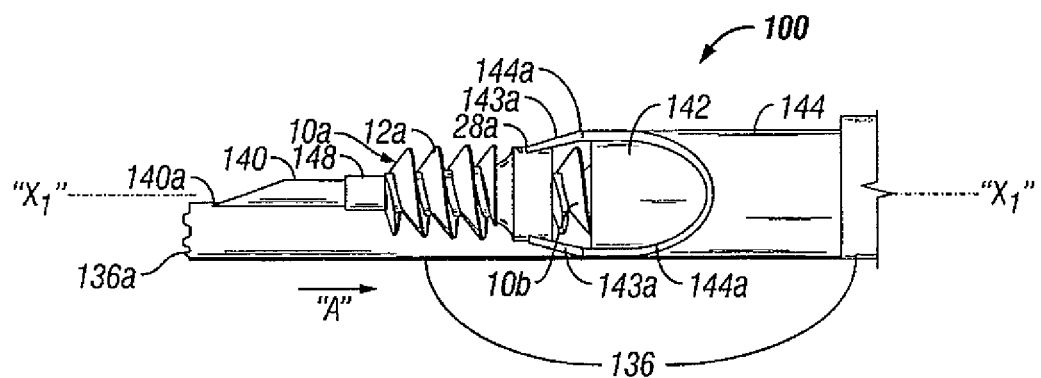
FIGS. 9-17 are partial cross-sectional side elevational views of the distal end of the screw fastener applier of FIGS. 5-8, illustrating a series of operational steps of the screw fastener applier for driving the absorbable screw fastener of FIGS. 1-4 into the target surgical site.
Figure 10:
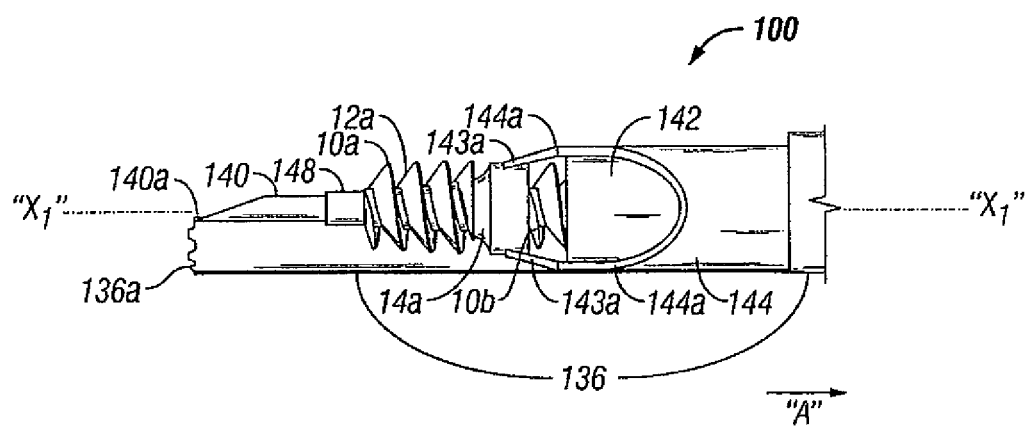

Pilot 140 functions as a guide to aid in the insertion of screw fastener 10 into tissue. Pilot 140 includes a sharpened distal tip 140a for tapping the mesh and underlying target tissue prior to insertion of screw fastener 10. Distal tip 140a of pilot 140 is shown with an angled tip. In an alternative embodiment, distal tip 140a of pilot 140 may be of various geometries. Referring to FIGS. 9-10, retaining feature 148, provided on pilot 140, holds a distal-most screw fastener 10a in place as will be described below. In a loaded position, fastener applier 100 includes at least one screw fastener 10 disposed in or retained in fastener retainer 142 such that pilot 140 extends through cannulated opening 18 of screw fastener 10. As explained above, slots 28 of head portion 14 of screw fastener 10 are engaged by respective tips 143a of fingers 144a of cylindrical driver 144. Tips 143a of fingers 144a of cylindrical driver 144 are configured and dimensioned to engage and/or be received in respective slots 28 formed in head portion 14 of screw fastener 10.

A method of inserting absorbable screw fastener 10, using fastener applier 100, will now be discussed. Referring to FIGS. 5, 6 and 9-17, distal tip 136a of outer tube 136 is initially placed against the mesh and/or the target tissue. Advantageously, crenellated tip 136a of outer tube 136 securely engages the mesh and helps to prevent movement of the mesh relative to the tissue. The user then pushes distal tip 136a of outer tube 136 against the target mesh or tissue. In so doing, a spring (not shown) is compressed allowing outer tube 136 to retract proximally, in the direction of arrow "A" (see FIG. 9), and thus unlocking a trigger lock (not shown).

As a safety feature, as seen in FIG. 10, pilot 140 remains within outer tube 136 even when outer tube 136 is fully retracted. This safety feature prevents accidental contact or pricking with distal tip 140a of pilot 140.

Figure 11:
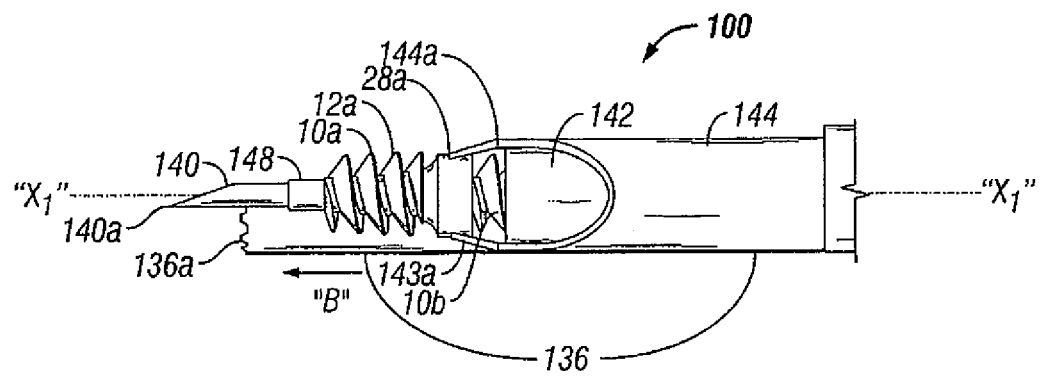
Figure 17:
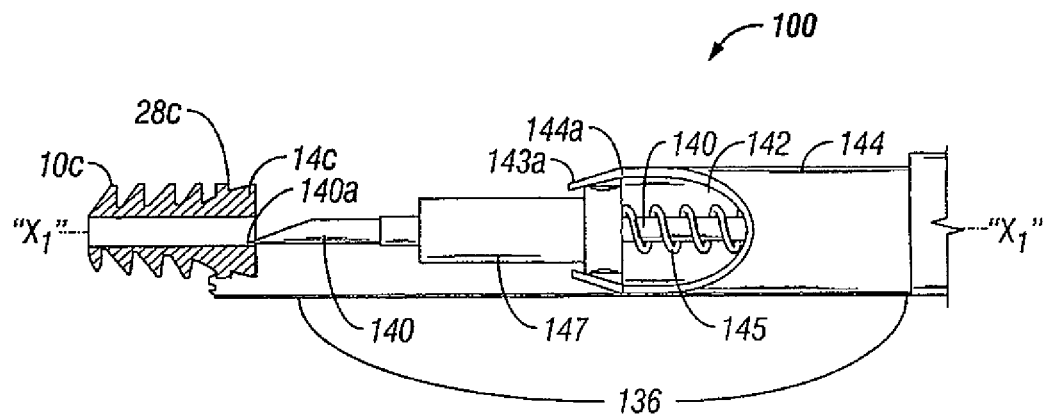

Referring now to FIGS. 6, 11 and 17, with outer tube 136 in the fully retracted position, fastener applier 100 is capable of firing screw fastener 10 therefrom. To drive and/or expel fastener(s) 10 from fastener applier 100, trigger 116 is drawn toward handle 114 against the bias of return spring 115. As trigger 116 is moved, teeth 117 on gear portions 121 of trigger 116 engage and rotate teeth 119 of trigger gear 123 clockwise, ultimately causing cylindrical driver 144, fastener retainer 142 and pilot 140 to be driven (axially in the direction of arrow "B") and rotated (about the longitudinal "X1" axis) until pilot 140 extends beyond distal tip 136a of outer tube 136 of fastener applier 100, as shown in FIG. 11. In one embodiment, pilot 140 extends beyond distal tip 136a of outer tube 136 by an amount approximately equal to 3 mm. Feed spring 145 acts on a plunger 147 to bias plunger 147 against the proximal-most screw fastener and maintain a force in the distal direction on the column of screw fasteners 10 disposed within fastener retainer 142.

Figure 12:
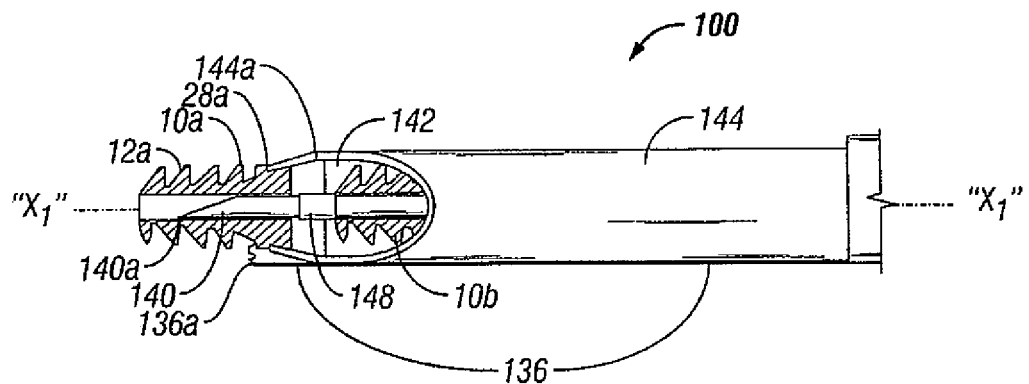

As shown in FIG. 12 and as will be discussed in greater detail below, once pilot 140 has stopped moving distally, cylindrical driver 144 and fastener retainer 142 continue to be driven and rotated distally until head portion 14 of a distal-most absorbable screw fastener 10a is substantially in line with distal tip 136a of outer tube 136 thus preventing insertion of distal-most screw fastener 10a beyond distal tip 136a of outer tube 136. As shown in FIG. 12, cylindrical driver 144 drives and rotates distal-most screw fastener 10a completely over and beyond retaining feature 148 of pilot 140. Additionally, retaining feature 148 acts as a stop to the distal advancement of an adjacent absorbable screw fastener 10b, adjacent distal-most screw fastener 10a, until adjacent screw fastener 10b is engaged and advanced by cylindrical driver 144.

Retaining feature 148 may be in the form of a C-ring, compressible O-ring, a crimp or bump in the cannulated lumen 18 (see FIG. 15A) or the like, wherein retaining feature 148 has an initial dimension which is greater than the dimension of cannulated lumen 18 of screw fastener 10. Accordingly, when distal-most screw fastener 10a initially engages or contacts retaining feature 148, since retaining feature 148 is sized to be larger than cannulated lumen 18, distal-most screw fastener 10a is prevented from passing. However, as the force being applied to distal-most screw fastener 10a is increased, retaining feature 148 is caused to be squeezed into cannulated lumen 18 as distal-most fastener 10a is advanced. Distal-most fastener 10a is forced entirely across retaining feature 148 such that the retaining feature passes through cannulated lumen 18 and exits a proximal end thereof. The column of screw fasteners, behind distal-most fastener 10a is then distally advanced by the force of feed spring 145. However, the force of feed spring 145 is not great enough to cause retaining feature 148 to be squeezed into the next screw fastener. Accordingly, retaining feature 148 prevents the distal advancement of the column of screw fasteners.

Figure 13:
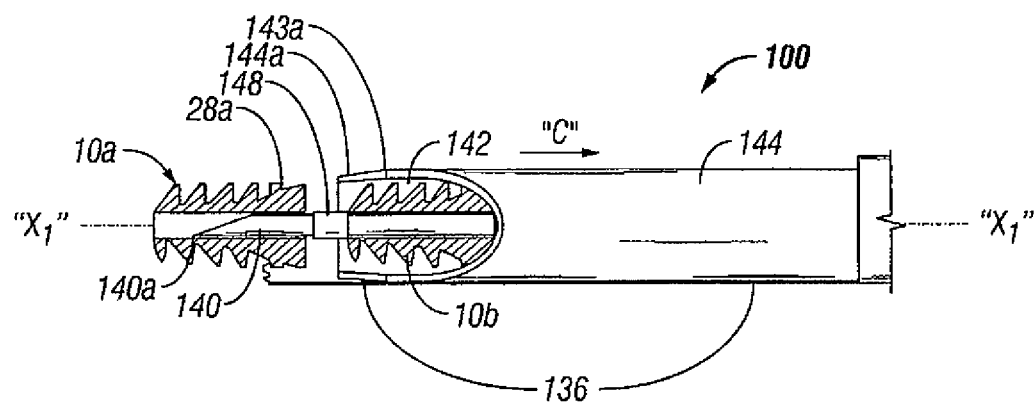

Once trigger 116 has been completely depressed and distal-most screw fastener 10a is driven through the mesh and into the tissue, the user releases trigger 116 and a two stage release cycle begins. Referring to FIG. 13, while fastener retainer 142 remains fixed in place, cylindrical driver 144 is retracted in a proximal direction (e.g., in the direction of arrow "C"). Cylindrical driver 144 is not rotated and drawn in a proximal direction so that distal-most fastener 10a is not unscrewed. As cylindrical driver 144 is retracted resilient fingers 144a deflect or cam radially outward as resilient fingers 144a slide over the tapered surface of slots 28a to disengage slots 28a of head portion 14a of distal-most screw fastener 10a and release distal-most screw fastener 10a. In addition, as cylindrical driver 144 is retracted resilient fingers 144a are cammed radially outward by their inter-engagement with fastener retainer 142. Cylindrical driver 144 may be retracted until a distal-most tip of resilient fingers 144a is substantially aligned with a distal-most edge of fastener retainer 142.

Figure 14:
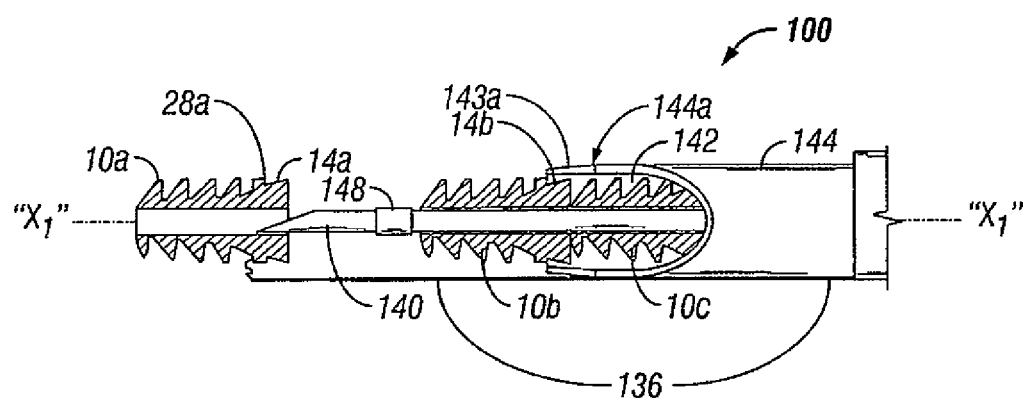

Referring now to FIG. 14, pilot 140 is proximally retracted until pilot 140 is disposed within outer tube 136 such that distal tip 140a of pilot 140 is not longer exposed. Additionally, cylindrical driver 144 and fastener retainer 142 are proximally retracted until tips 143a of resilient fingers 144a of cylindrical driver 144 are aligned with slots 28b formed in head portion 14b of adjacent screw fastener 10b. In an alternative embodiment, cylindrical driver 144 and pilot 140 may retract independently of one another or simultaneously.

Figure 15:
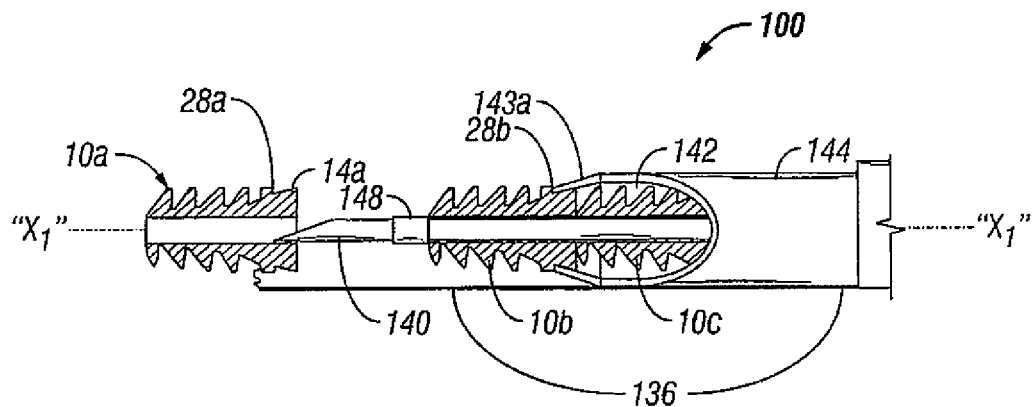
Figure 15A:
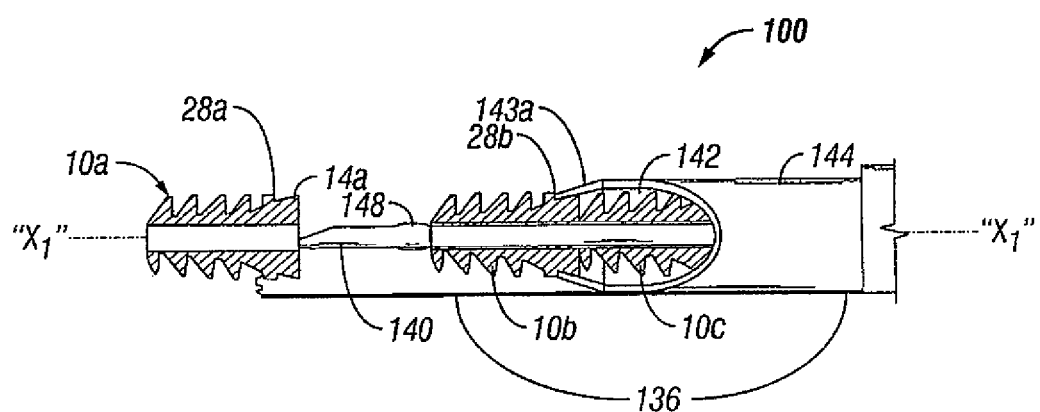
Figure 16:
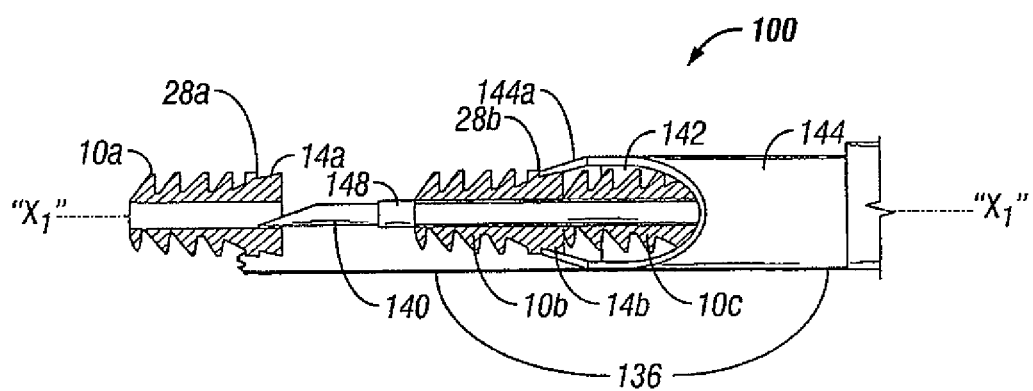

Referring now to FIG. 15, while screw fastener 10b is maintained in position by retaining feature 148, fastener retainer 142 is proximally retracted, to its starting position, as shown in FIG. 8, so that tips 143a of resilient fingers 144a of cylindrical driver 144 return to their un-deflected position and engage slots 28b of head portion 14b of adjacent screw fastener 10b. Since fastener retainer 142 has a longer stroke to return to its starting position as compared to cylindrical driver 144 resilient fingers 144a of cylindrical driver 144 flex back down and engage adjacent screw fastener 10b. Referring to FIG. 16, outer tube 136 is returned to its starting position, as shown in FIGS. 9 and 17. In alternative embodiments, distal movement of outer tube 136 to its starting position can be accompanied by an audible and/or tactile response heard/felt by the end user. In alternative embodiments cylindrical driver 144 and fastener retainer 142 can proximally retract together.

In an embodiment, housing 112 may be fabricated to have a reusable handle portion 114 and trigger 116 that can be re-sterilized, and a disposable elongated tubular portion 118. Thus, upon discharge of all the screw fasteners 10 elongated tubular portion 118 would be discarded and replaced, housing portion 112 would be sterilized and reused up to a limited number of procedures.

In other embodiments, revolving means to cause cylindrical driver 144 to rotate may include a single knob connected to a rotator which can be turned by hand. Additionally, the revolving means may include a rack and gear structure or a set of beveled gears.

Figure 18:
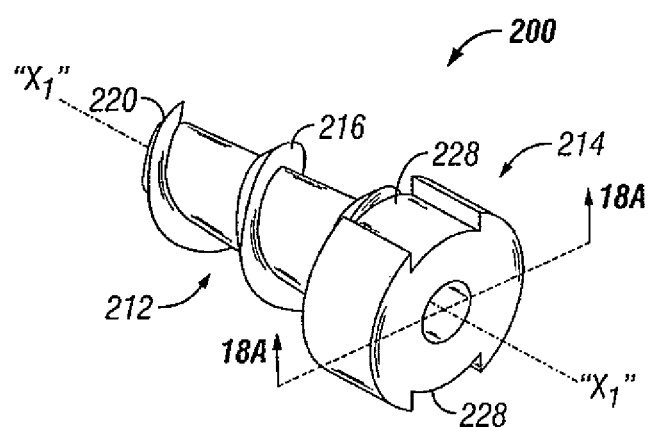
FIG. 18 is a perspective view of another embodiment of an absorbable screw fastener of the present disclosure.
Figure 18A:
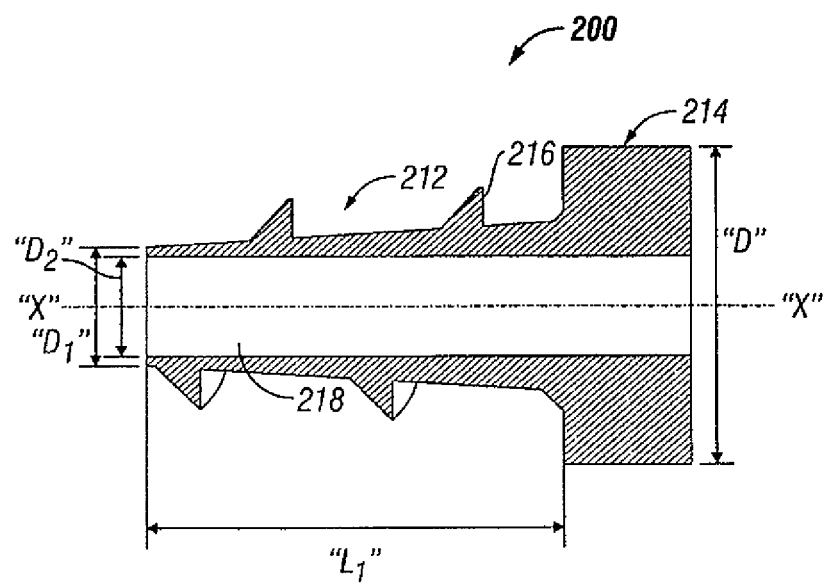
FIG. 18A is a longitudinal cross-sectional view of the absorbable screw fastener of FIG. 18 taken along line 18A-18A of FIG. 18.
Figure 18B:
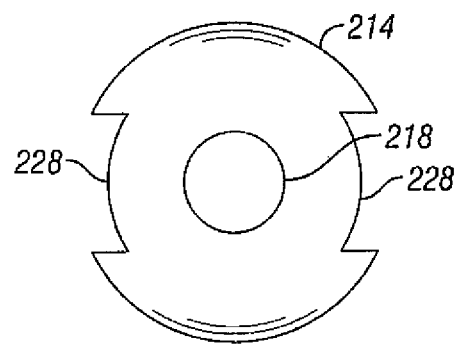
FIG. 18B is a top view of the absorbable screw fastener of FIGS. 18 and 18A.

FIGS. 18, 18A and 18B present another possible embodiment of the absorbable screw fastener. Screw fastener 200 is similar to screw fastener 10 and will only be discussed in detail to the extent necessary to identify differences in construction and/or operation. In one embodiment, body portion 212 of screw fastener 200 has a uniform distance along at least a portion of, desirably along its entire, length which is equal to inner distance "D2". Also, distance "D1" of body portion 212 may be tapered from a narrow, blunt distal end 220 to a larger proximal end where it transitions into the outside diameter of proximal head portion 214 to increase torque strength. The gradual taper along body portion 212 allows a small footprint of screw fastener 200 when entering the mesh, and growing radially outward along the length of body portion 212 for better rates of absorption into the body and then transitions into the outside diameter of head portion 214 to help resist torque. In addition, slots 228, formed in head portion 214 are parallel to the longitudinal axis "X" axis and extend the entire thickness of head portion 214.

Figure 19:
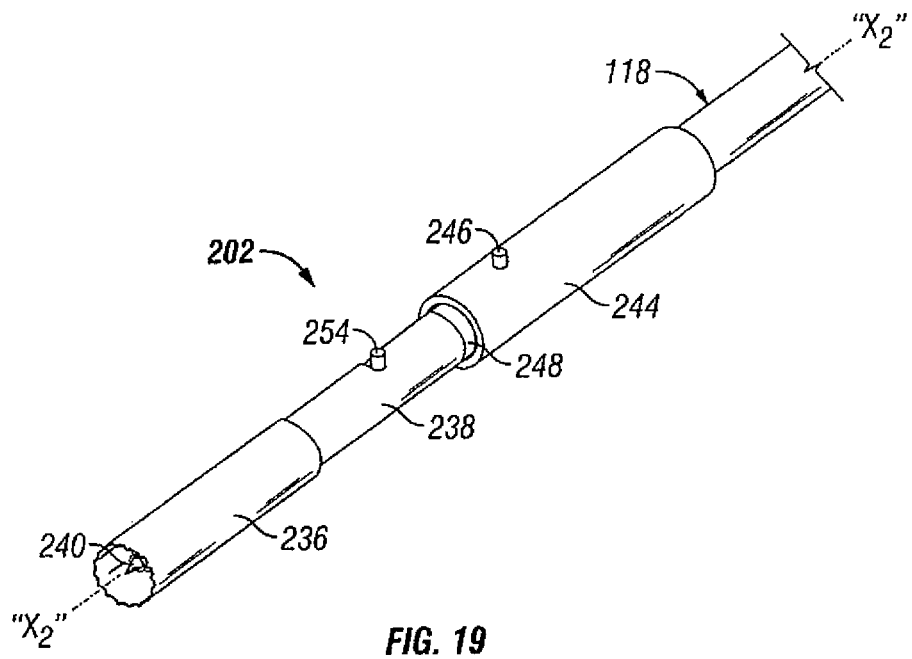
FIG. 19 is a perspective view of a distal end of a screw fastener applier according to another embodiment of the present disclosure, with an end effector operatively secured thereto.
Figure 20:
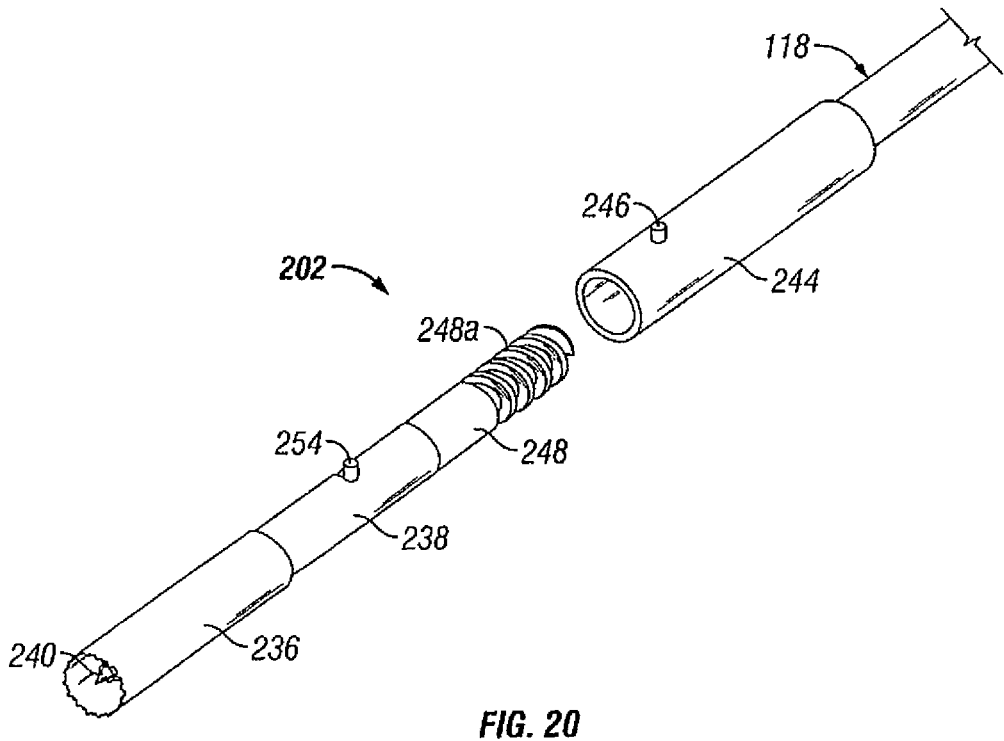
FIG. 20 is a perspective view of the distal end of the screw fastener applier of FIG. 19, with the end effector separated or disconnected therefrom.
Figure 21:
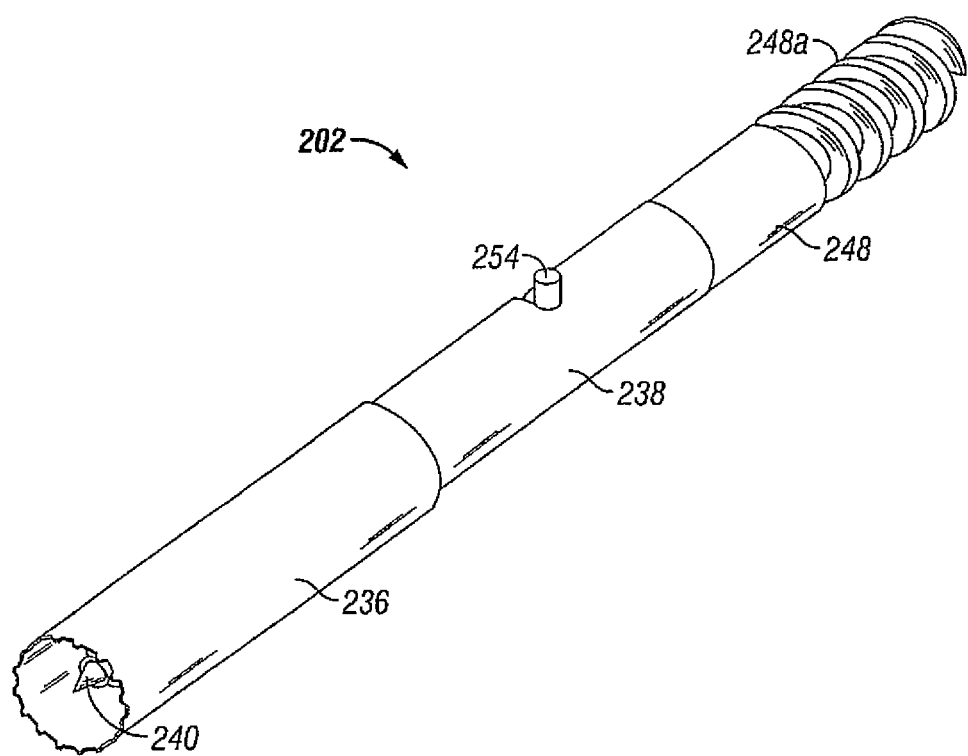
FIG. 21 is a perspective view of the assembled cam spiral sub-assembly, inner tube sub-assembly and outer tube of the end effector according to the present disclosure.

With reference to FIGS. 19-21, an end effector for engagement with a distal end of elongated tubular portion 118 of fastener applier 100, to be used for the application of screw fasteners 10 or 200 or for retaining screw fasteners 10 or 200, is generally designated as 202. End effector 202 may take the form of a disposable loading unit (DLU) or single use loading unit (SULU) which retains a load of fasteners 10 or 200 therein, and which may be disposed of or replaced or may be sterilized, re-loaded and reused.

Referring initially to FIGS. 19-21, end effector 202 includes an outer tube 236, defining longitudinal axis "X2" and housing an inner tube assembly 238 for retaining screw fasteners 200 therein, a cam spiral driver 244 supported on the distal end of tubular portion 118, a pin 254 and a cam spiral sub-assembly 248 disposed in inner tube assembly 238 and operatively connected to cam spiral drive 244.

End effector 202 is attached to or formed integral with the distal end of elongated tubular portion 118 of fastener applier 100 such that when control trigger 116 of fastener applier 100 is drawn toward handle 114, cam spiral driver 244 rotates (similar to the rotation of cylindrical driver 144 described above). Cam spiral sub-assembly 248 includes a helical thread 248a, which mates with and receives a pin 246 of cam spiral driver 244 so that when cam spiral driver 244 rotates, cam spiral sub-assembly 248 rotates and translates, as discussed in detail hereinbelow.

Figure 22:
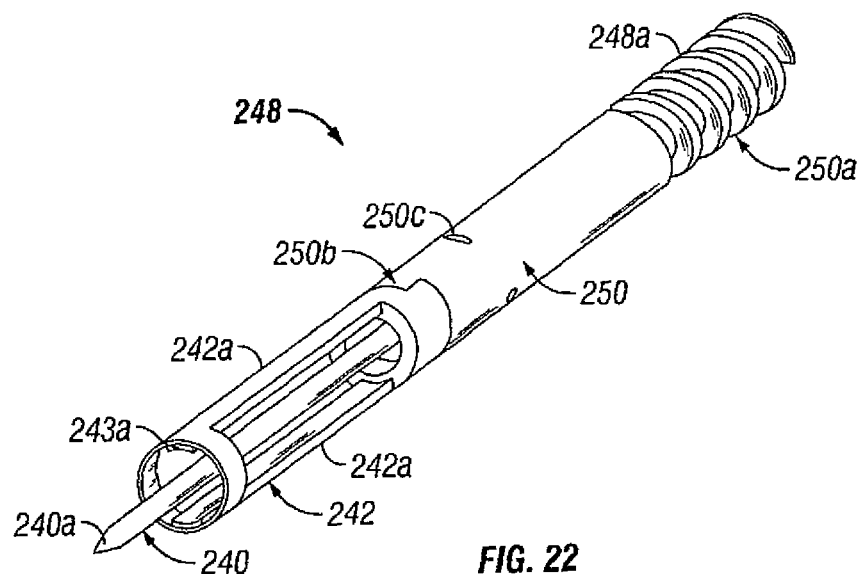
FIG. 22 is a perspective view of a cam spiral sub-assembly of the end effector of FIG. 21 with the outer tube and inner tube sub-assembly removed therefrom.
Figure 23:
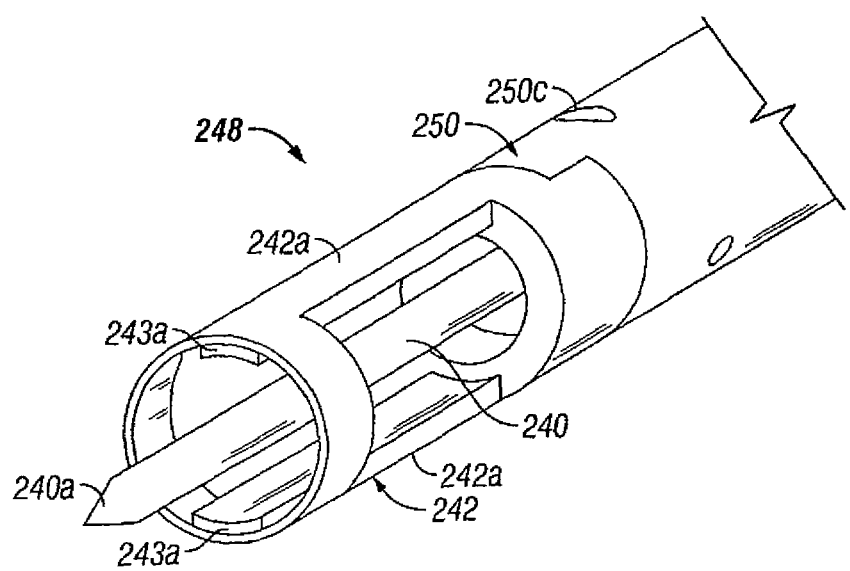
FIG. 23 is a further perspective view of the cam spiral sub-assembly of FIG. 22.
Figure 24:
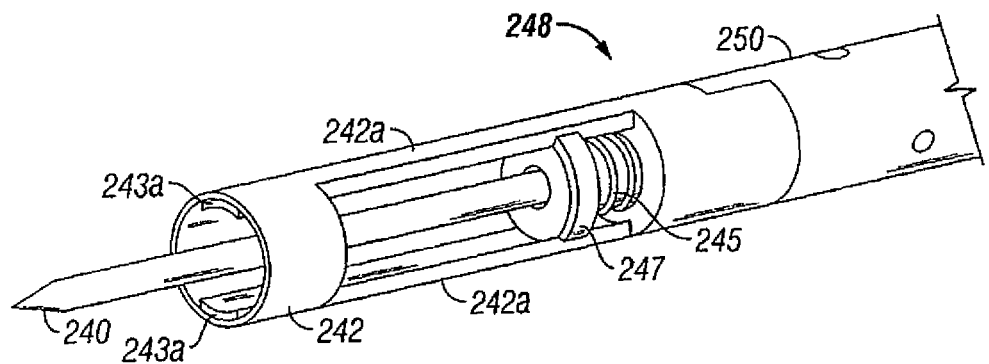
FIG. 24 is a perspective view of the cam spiral sub-assembly of FIGS. 22 and 23, with a pusher and feed spring shown operatively associated therewith.

Referring to FIGS. 22 and 23, cam spiral sub-assembly 248 will be discussed in detail. Cam spiral sub-assembly 248 includes a cam spiral 250 having a proximal end 250a defining a helical thread 248a, pilot 240 extending longitudinally from a distal end 250b of cam spiral 250, and a fastener retainer 242 operatively supported on distal end 250b of cam spiral 250. Cam spiral sub-assembly 248 is assembled in such a manner that upon rotation of cam spiral 250, pilot 240 and fastener retainer 242 are similarly rotated. In alternative embodiments, cam spiral sub-assembly 248 may be fabricated as a single part/component. Fastener retainer 242 may include a pair of opposed longitudinally extending rails 242a which act as retainers or guides for screw fasteners 200. A distal end 243a of rails 242a will also act as a driver for screw fasteners 200, as will be described hereinbelow. Desirably, a distal end 240a of pilot 240 extends distally of distal end 243a of rails 242a and fastener retainer 242. A pin 254 (see for instance FIG. 21) is received in and extends radially from a slot 250c formed in cam spiral 250.

Figure 25:
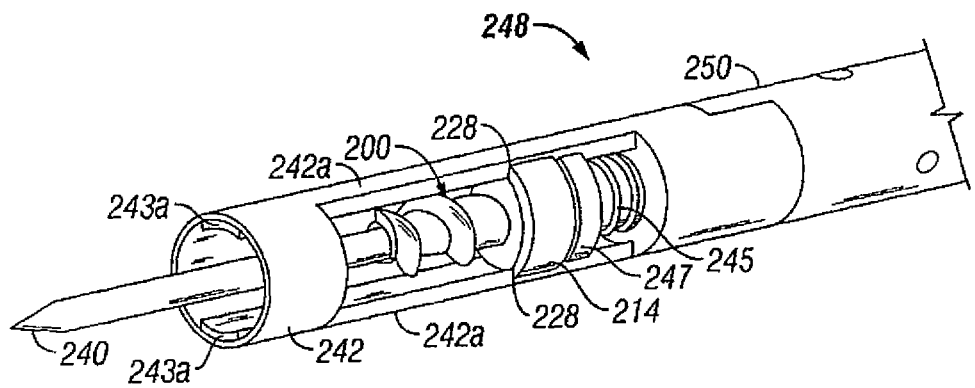
FIG. 25 is a perspective view of the cam spiral sub-assembly of FIG. 24, illustrating a screw fastener operatively associated therewith.
Figure 26:
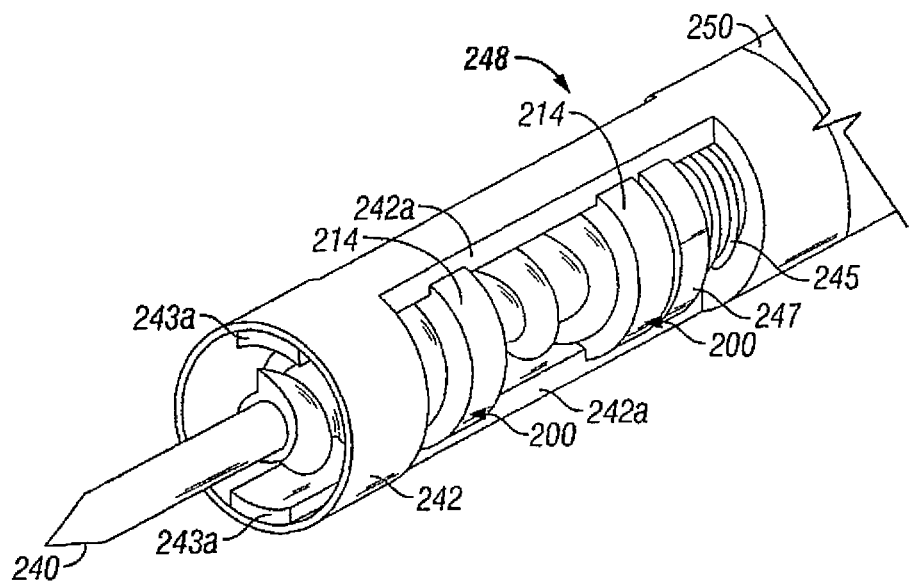
FIG. 26 is a perspective view of the cam spiral sub-assembly of FIGS. 24 and 25, with a pair of screw fasteners operatively associated therewith.
Figure 27:
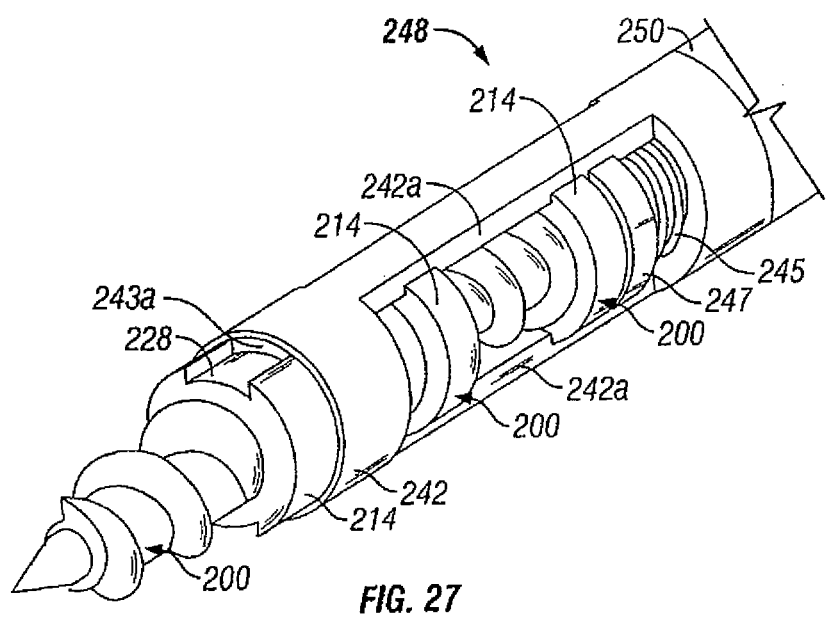
FIG. 27 is a perspective view of the cam spiral sub-assembly of FIGS. 24-26, with at least three screw fasteners operatively associated therewith.

A seen in FIGS. 24-27, cam spiral sub-assembly 248 further includes a feed spring 245 and a screw fastener pusher 247, each disposed on pilot 240 and within fastener retainer 242. As shown in FIGS. 25-27, rails 242a of fastener retainer 242 orients screw fasteners 200 by engaging respective slots 228 in head portion 214 of screw fastener 200. Desirably, feed spring 245 is disposed between screw fastener pusher 247 and cam spiral 250. As such, feed spring 245 biases pusher 247 in a distal direction.

Multiple screw fasteners 200 may be retained in or operatively associated with cam spiral sub-assembly 248, for example, one (1) as seen in FIG. 25, two (2) as seen in FIG. 26, or three (3) as seen in FIG. 27. While one to three screw fasteners 200 are shown in FIGS. 25-27, it is understood that the present device may be used with or may accommodate any number of screw fasteners 200.

Figure 28:
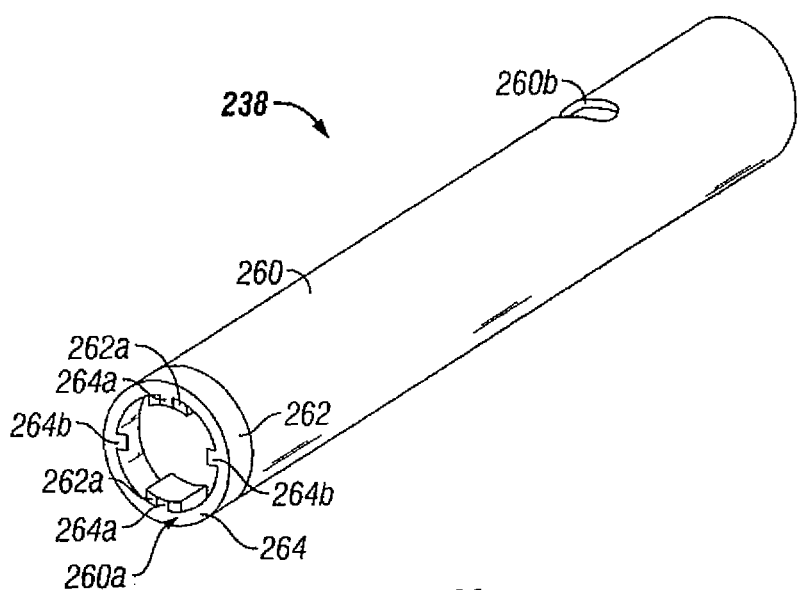
FIG. 28 is a perspective view of the inner tube sub-assembly of the end effector of FIGS. 21 and 28.

Referring now to FIG. 28, in an alternate embodiment or additionally, inner tube sub-assembly 238 includes a cylindrical body 260, a torque ring 262 operatively connected to a distal end 260a thereof, and a retaining ring 264 operatively connected to torque ring 262. Cylindrical body 260, includes a transversely oriented rotational slot 260b formed therein for slideably receiving pin 254 extending from cam spiral 250. Rotational slot 260b limits the movement of pin 254 and, in turn, the rotation of cam spiral driver 244. Rotational slot 260b may be sized to limit the rotation to about 90 degrees. With continued reference to FIG. 28, torque ring 262 includes a pair of diametrically opposed engagement features 262a extending radially inward therefrom. Engagement features 262a are desirably sized to mate with corresponding slots 228 of head portion 214 of screw fastener 200. Retaining ring 264 includes two pair of diametrically opposed tabs 264a, 264b extending radially inward therefrom. Tabs 264a, 264b may be offset by about 90 degrees relative to one another. Desirably, one pair of tabs 264a is axially aligned with engagement features 262a of torque ring 262. Tabs 264a, 264b hold distal screw fastener 200 in place and prevent feed spring 245 of cam spiral sub-assembly 248 from driving all the internal screw fasteners 200 out from the instrument in one rapid fire sequence.

Inner tube sub-assembly 238 may be constructed from several different components mounted or otherwise operatively connected to one another to form a unitary inner tube sub-assembly 238 or may be manufactured as a single component.

Figure 29:
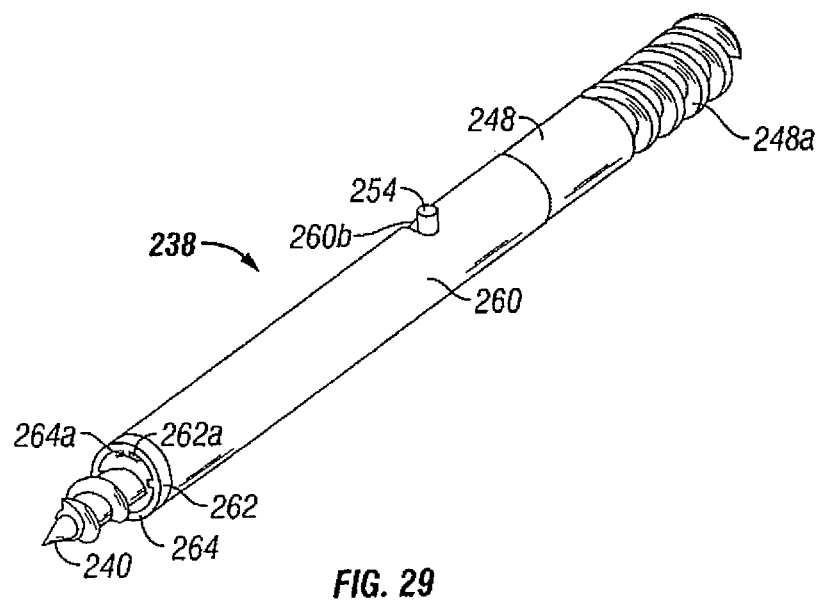
FIG. 29 is a perspective view of the cam spiral sub-assembly of FIG. 27 operatively disposed within the inner tube sub-assembly of FIG. 28, while in a first position.
Figure 30:
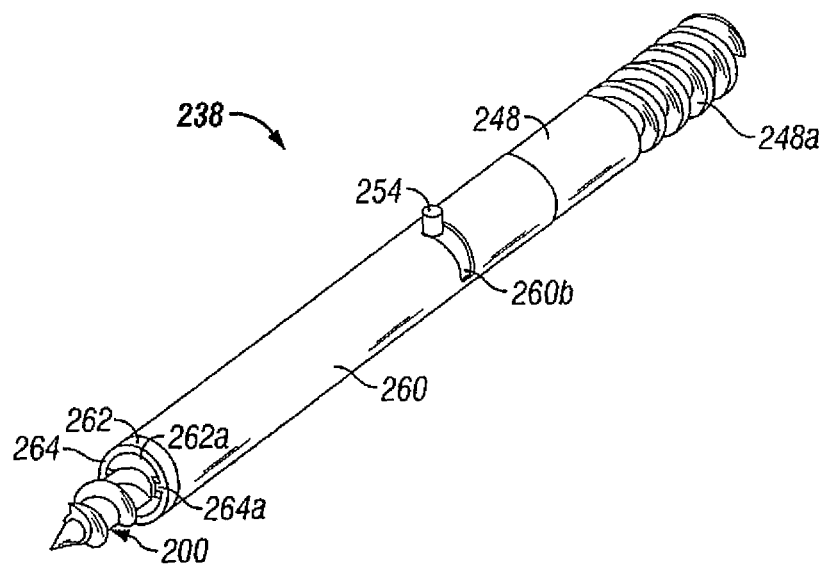
FIG. 30 is a perspective view of the cam spiral sub-assembly and inner tube sub-assembly of FIG. 29, while in a second position.
Figure 31:
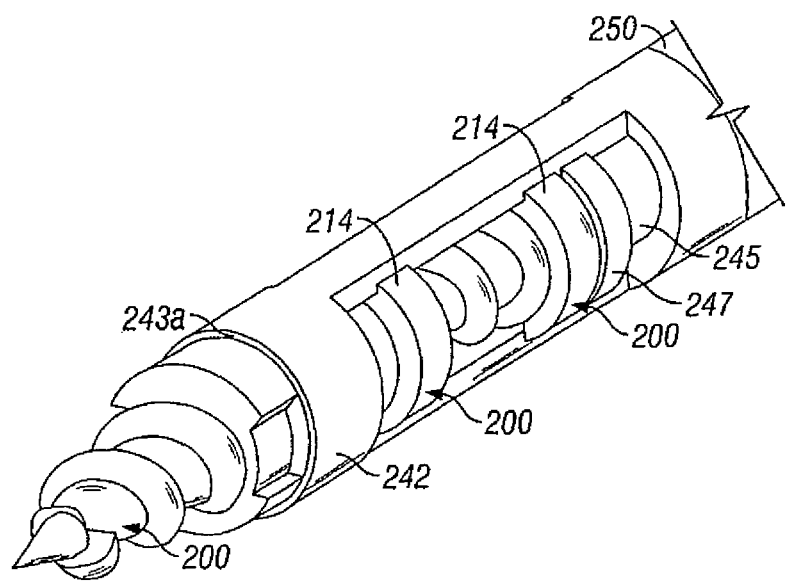
FIG. 31 is a perspective view of the cam spiral sub-assembly of FIG. 27, while in the second position of FIG. 30.

Referring now to FIGS. 29 and 30, inner tube sub-assembly 238 is shown operatively associated with (e.g., rotatably supported on) cam spiral sub-assembly 248. As described above, pin 254 extends through rotational slot 260b of inner tube sub-assembly 238. Accordingly, inner tube sub-assembly 238 and cam spiral sub-assembly 248 act as one unit when cam spiral sub-assembly 248 is activated, as will be described in greater detail below.

In FIG. 29, inner tube subassembly 238 is shown in a first position with respect to cam spiral sub-assembly 248 and with pin 254 located at one end of rotational slot 260. In FIG. 30, inner tube sub-assembly is shown in a second position with respect to cam spiral sub-assembly 248 and with pin 254 located at an opposite end of rotational slot 260.

Figure 32:
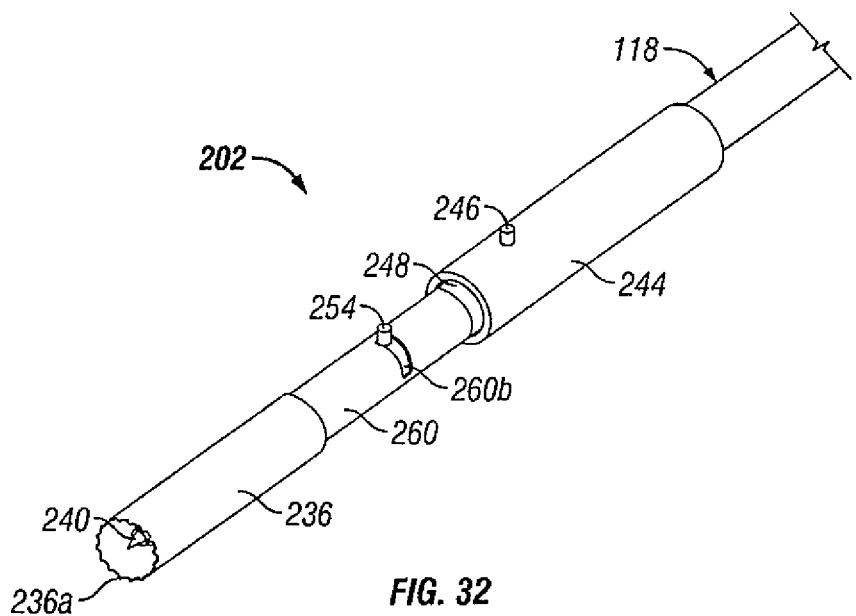
FIGS. 32-36 illustrate a series of operational steps of the surgical fastener applier including the end effector of FIGS. 19-31 for driving the absorbable screw fastener of FIGS. 18, 18A and 18B into the target surgical site.
Figure 33:
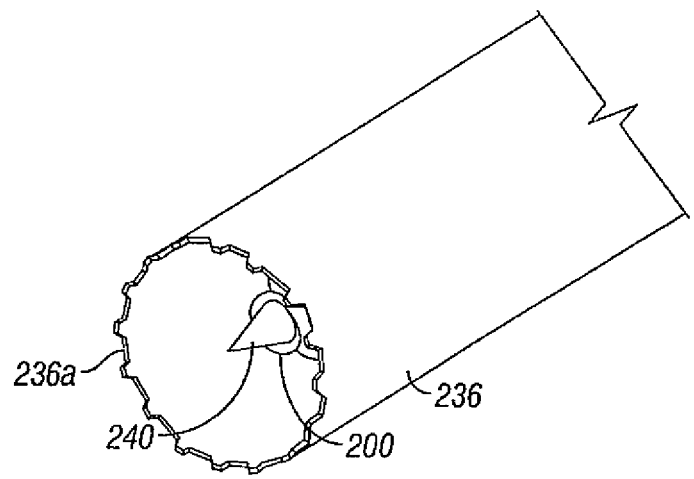

Turning now to FIGS. 31-36, a method of inserting absorbable screw fastener 200 or 10 will be discussed. Referring to FIGS. 32 and 33, a distal tip 236a (shown crenellated) of outer tube 236 is initially placed against the mesh and/or the target tissue. In so doing, distal tip 236a of outer tube 236 helps to maintain outer tube 236 firmly connected to the mesh and keeps the mesh taught.

Figure 34:
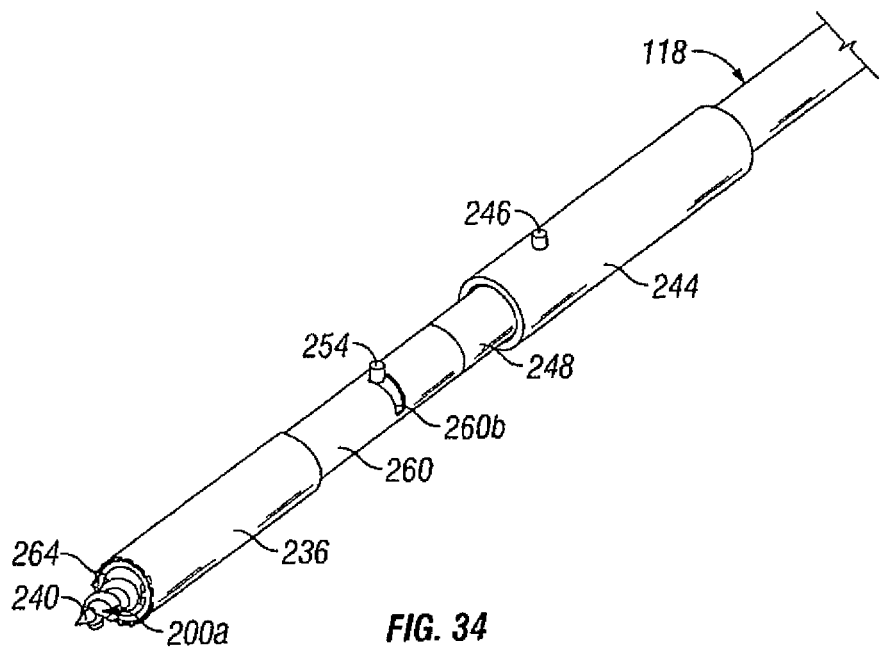
Figure 35:
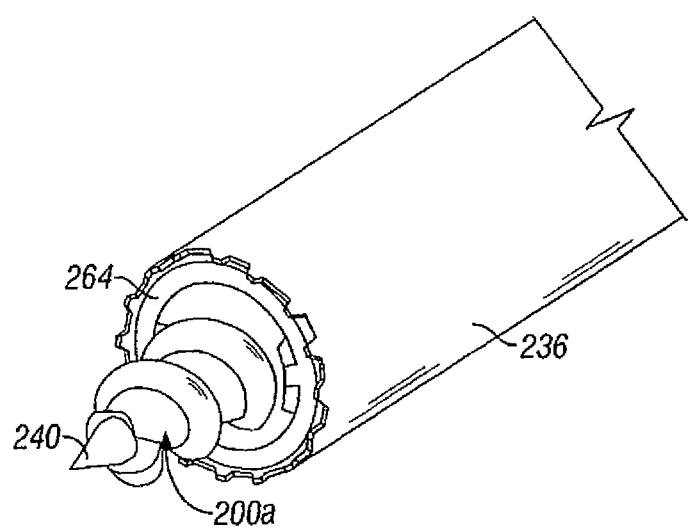

Next, the trigger of the fastener applier is actuated (e.g., squeezed) to rotate cam spiral driver 244 and to rotate and translate cam spiral sub-assembly 248 and inner tube sub-assembly 238. Holding outer tube 236 in a stationary position, a distal-most screw fastener 200a is advanced distally as shown in FIGS. 34 and 35. In particular, as cam spiral sub-assembly 248 is rotating and translating to drive distal-most screw fastener 200a forward, inner tube sub-assembly 238 rotates distal-most screw fastener 200a.

Figure 36:
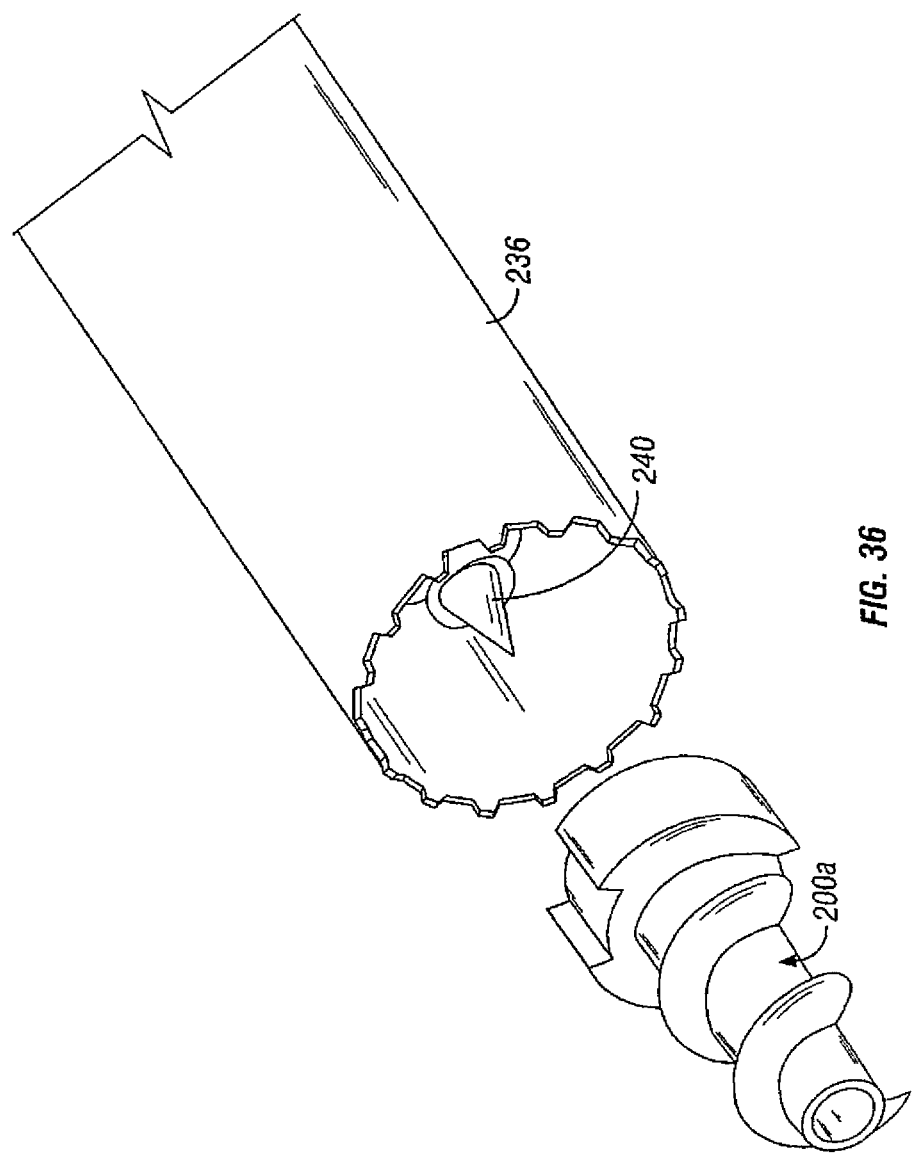

As seen in FIG. 36, cam spiral sub-assembly 248 (see FIG. 34) will drive distal screw fastener 200a an amount sufficient to push distal-most screw fastener 200a beyond tabs 264b of retaining ring 264 (see FIG. 28) and thus releasing distal-most screw fastener 200a from the remainder of the fastener applier.

Desirably, when the trigger of the fastener applier is released, all internal sub-assemblies retract and reorient themselves, thus allowing feed spring 245 to advance the next screw fastener into torque ring 254.

Figure 37:
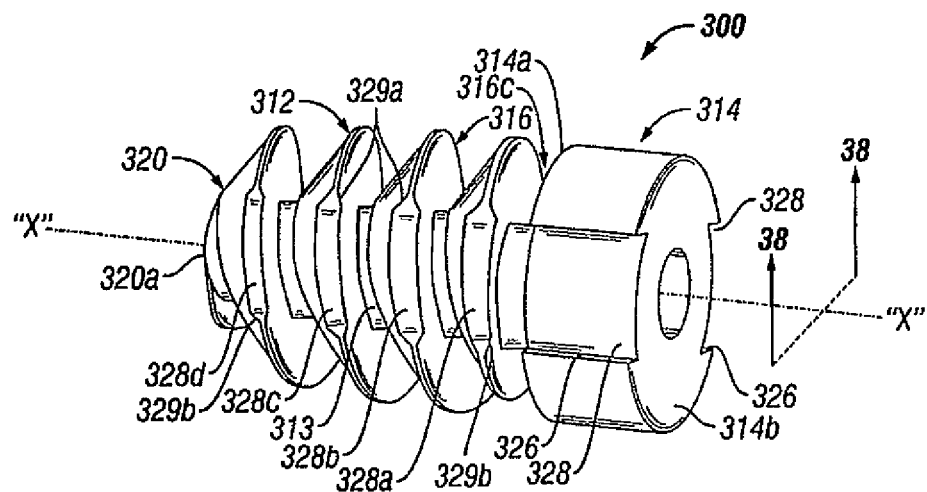
FIG. 37 is a rear perspective view of an absorbable screw fastener according to a further embodiment of the present disclosure.
Figure 38:
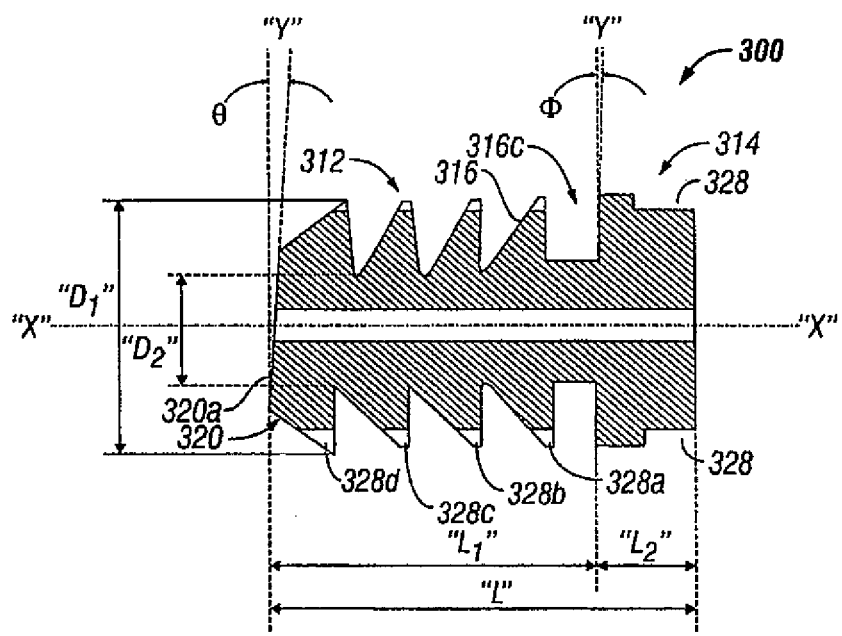
FIG. 38 is a longitudinal cross-sectional view of an absorbable screw fastener of the present disclosure.

Turning now to FIGS. 37 and 38, another possible embodiment of the absorbable screw fastener, is shown generally as 300. Screw fastener 300 is similar to screw fastener 10 and will only be discussed in detail to the extent necessary to identify differences in construction and/or operation.

Screw fastener 300 includes a body portion 312 defining a longitudinal axis "X" and a substantially circular head portion 314 disposed on a proximal end of body portion 312. Body portion 312 includes a helical thread 316 extending along a length thereof, and terminates in a distal end 320. In the present embodiment, helical thread 316 is tapered to tangency at the distal end for ease of insertion purposes. The proximal end of helical thread 316 stops before a distal surface of head portion 314 to create gap 316c in which the mesh (not shown) may be received.

Figure 38A:
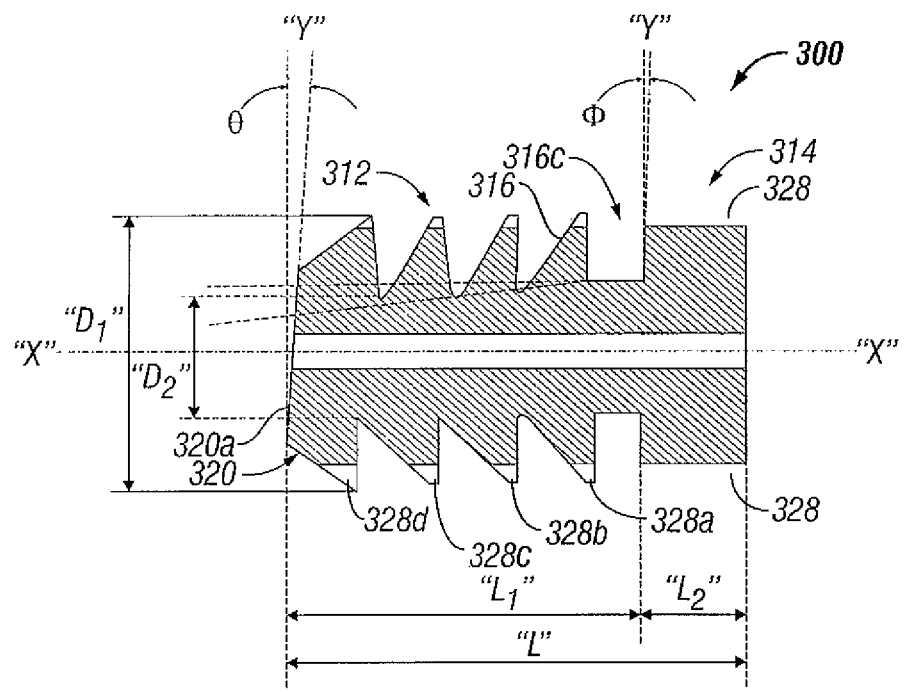
FIG. 38A is a longitudinal cross-sectional view of the absorbable screw fastener of FIG. 37 taken along line 38-38 of FIG. 37.

Distal end 320 of body portion 312 defines a distal surface 320a which is angled with respect to the "X" axis by an angle Θ. In one embodiment, angle Θ of distal surface 320a is from about 5° to about 15° with respect to an axis "Y" which is orthogonal to the "X" axis. In yet another embodiment, angle Θ is about 9°. Further, body portion 312 includes a center shaft 313 extending along a length thereof. In one embodiment, center shaft 313 is tapered, with respect to the "X" axis by an angle β, to have a smaller distal end and a larger proximal end in order to increase the ease of insertion of screw fastener 300, as shown in FIG. 38A.

With continued reference to FIGS. 37 and 38, head portion 314 includes driver receiving recesses or structure, in the form of slots 328, formed in an outer radial surface of head portion 314. Slots 328 are configured to transmit torque to screw fastener 300. In one embodiment, a pair of diametrically opposed slots 328 are formed in head portion 314. Each slot 328 may be parallel to the longitudinal "X" axis, and extend through a distal surface 314a and a proximal surface 314b of head portion 314. Slots 328 extend the entire length of screw fastener 300 to define corresponding slots 328a-328d formed in helical thread 316.

In one embodiment, head portion 314 has a low profile, i.e., head portion 314 has a length "L2" which is about 1.5 mm and a distance of about 3.81 mm. Also, body portion 312 may have a length "L1" which is about 5.0 mm. As such, the overall length "L" of screw 300 is about 6.5 mm.

Alternatively or additionally, it is envisioned that a torque transmitting feature may be provided on slots 328, in the form of shoulders 326, the torque transmitting feature allowing for screw fastener 300 to be rotated.

Distal surface 314a may also be angled as shown with respect to the "X" axis by an angle Φ. In one embodiment, angle Φ of distal surface 314a is from about 5° to about 15° with respect to an axis "Y" which is orthogonal to the "X" axis. In yet another embodiment, angle Φ is about 9°. The angle of distal surface 314a is provided to help with the removal of screw fastener 300 in the event that screw fastener 300 needs to be removed from the surgical site.

A space or gap 316c may be provided between a proximal thread run-out and distal surface 314a of head portion 314. Gap 316c allows for the surgical mesh to rest therein. It is envisioned that the pitch of thread 316 may be larger or smaller depending on the particular surgical procedure.

As seen in FIG. 37, each slot 328a-328d includes a radiused distal or leading edge 329a and a radiused proximal or trailing edge 329b. Radiused leading edge 329a and radiused trailing edge 329b help to facilitate insertion of and removal of screw fastener 300 into and from the surgical site.

From the foregoing, it will be appreciated that the screw fastener and fastener applier of the present invention cooperate to securely attach a fastener with high retentive surface area, to tissue, from one direction, through the utilization of a fastener applier having a simpler design. It is also to be appreciated that the present invention may be utilized in a number of applications including ligating tissue, hernia mesh repair, bladder neck suspension, arthroscopic knee surgery, and in conjunction with implant drug delivery systems or procedures involving positioning of surgical or implantable devices in patients.

While several particular forms of the invention have been illustrated and described, it will also be apparent that various modifications can be made without departing form the spirit and scope of the invention.

Thus, it should be understood that various changes in form, detail and application of the present invention may be made without departing form the spirit and scope of the invention.

What is claimed is:

1. An instrument for firing a plurality of fasteners loaded therein into a surgical mesh overlying a target tissue site, the instrument comprising:
    a handle assembly having a trigger mechanism;
    an elongate endoscopic distal portion supported on and extending from the handle assembly, the endoscopic distal portion configured to retain the plurality of fasteners therein, the endoscopic distal portion defining a distal tip through which each fastener exits; and
    a mesh securing feature projecting distally from the distal tip of the endoscopic distal portion, wherein the mesh securing feature is a crenellated tip such that the mesh securing feature increases friction between the distal tip of the endoscopic distal portion and the surgical mesh during a firing of the instrument.

2. The instrument according to claim 1, wherein the instrument includes a driver/torque subassembly disposed within the endoscopic distal portion and being movable relative to the endoscopic distal portion.

3. The instrument according to claim 1, wherein the endoscopic distal portion includes an outer tube.

4. The instrument according to claim 2, wherein the driver/torque sub-assembly defines two flexible tabs in a distal end of the drive/torque subassembly.

5. The instrument according to claim 3, wherein the outer tube is biased to a distally advanced position.

6. The instrument according to claim 5, further comprising a pilot disposed within the outer tube, the pilot having a tapered surface on its distal end.

7. The instrument according to claim 1, wherein the endoscopic distal portion includes a fastener retainer dimensioned to receive the plurality of fasteners.

8. The instrument of claim 1, wherein the crenellated tip includes crenellations that engage the surgical mesh to limit movement of the surgical mesh while at least one of the plurality of fasteners is fired through the surgical mesh and into the target tissue site.

9. An instrument for firing a plurality of fasteners loaded therein into a surgical mesh overlying a target tissue site, the instrument comprising:
    a handle assembly having a trigger mechanism;
    an elongate endoscopic distal portion supported on and extending from the handle assembly, the endoscopic distal portion configured to retain the plurality of fasteners therein, the endoscopic distal portion defining a distal tip through which each fastener exits, the endoscopic distal portion including a mesh securing feature projecting distally from the distal tip thereof, wherein the mesh securing feature is a crenellated tip such that the mesh securing feature increases friction between the distal tip of the endoscopic distal portion and the surgical mesh during a firing of the instrument; and a plurality of fasteners loaded in the endoscopic distal portion.

10. The instrument according to claim 9, wherein the instrument includes a driver/torque subassembly disposed within the endoscopic distal portion and being movable relative to the endoscopic distal portion.

11. The instrument according to claim 9, wherein the endoscopic distal portion includes an outer tube.

12. The instrument according to claim 10, wherein the driver/torque sub-assembly defines two flexible tabs in a distal end of the drive/torque subassembly.

13. The instrument according to claim 11, wherein the outer tube is biased to a distally advanced position.

14. The instrument according to claim 13, further comprising a pilot disposed within the outer tube, the pilot having a tapered surface on its distal end.

15. The instrument according to claim 9, wherein the endoscopic distal portion includes a fastener retainer dimensioned to receive the plurality of fasteners.

16. The instrument of claim 9, wherein the crenellated tip includes crenellations that engage the surgical mesh to limit movement of the surgical mesh while at least one of the plurality of fasteners is fired through the surgical mesh and into the target tissue site.

\* \* \* \* \*